US011421211B2

(12) United States Patent
Mingozzi et al.

(10) Patent No.: US 11,421,211 B2
(45) Date of Patent: Aug. 23, 2022

(54) ACID-ALPHA GLUCOSIDASE VARIANTS AND USES THEREOF

(71) Applicants: GENETHON, Evry (FR); SORBONNE UNIVERSITE, Paris (FR); DUKE UNIVERSITY, Durham, NC (US)

(72) Inventors: Federico Mingozzi, Paris (FR); Giuseppe Ronzitti, Paris (FR); Dwight D. Koeberl, Durham, NC (US); Sang-Oh Han, Cary, NC (US)

(73) Assignees: GENETHON, Evry (FR); SORBONNE UNIVERSITÉ, Paris (FR); DUKE UNIVERSITY, Durham, NC (US)

( * ) Notice: Subject to any disclaimer, the term of this patent is extended or adjusted under 35 U.S.C. 154(b) by 433 days.

(21) Appl. No.: 16/332,373

(22) PCT Filed: Sep. 12, 2017

(86) PCT No.: PCT/EP2017/072942
§ 371 (c)(1),
(2) Date: Mar. 12, 2019

(87) PCT Pub. No.: WO2018/046772
PCT Pub. Date: Mar. 15, 2018

(65) Prior Publication Data
US 2019/0390184 A1 Dec. 26, 2019

(30) Foreign Application Priority Data

Sep. 12, 2016 (EP) .................................... 16306148

(51) Int. Cl.
*C12N 15/86* (2006.01)
*C12N 9/24* (2006.01)
*C12N 9/26* (2006.01)
*A61K 38/47* (2006.01)

(52) U.S. Cl.
CPC ............ *C12N 9/2408* (2013.01); *A61K 38/47* (2013.01); *C12N 15/86* (2013.01); *C12Y 302/0102* (2013.01); *C12N 2750/14132* (2013.01); *C12N 2750/14143* (2013.01)

(58) Field of Classification Search
CPC ................................ C12N 9/24; C12N 9/2408
See application file for complete search history.

(56) References Cited

U.S. PATENT DOCUMENTS

| 9,873,868 B2* | 1/2018 | Koeberl ................... A61P 3/00 |
| 10,556,015 B2* | 2/2020 | Zhang ................... A61K 47/64 |
| 10,731,177 B2* | 8/2020 | Vandendriessche ........................ A61K 48/0075 |
| 2019/0390225 A1 | 12/2019 | Mingozzi et al. |
| 2021/0040503 A1 | 2/2021 | Mingozzi et al. |

FOREIGN PATENT DOCUMENTS

| WO | WO 2004/064750 | 8/2004 |
| WO | WO 2013/192317 | 12/2013 |
| WO | WO 2018/046774 | 3/2018 |
| WO | WO 2018/046775 | 3/2018 |

OTHER PUBLICATIONS

Corti, M. et al. "Evaluation of Readministration of a Recombinant Adeno-Associated Virus Vector Expressing Acid Alpha-Glucosidase in Pompe Disease: Preclinical to Clinical Planning" *Human Gene Therapy Clinical Development*, Sep. 2015, pp. 185-193, vol. 26, No. 3.
Doerfler, P. A. et al. "Copackaging of Multiple Adena-Associated Viral Vectors in a Single Production Step" *Human Gene Therapy Methods*, Oct. 2014, pp. 269-276, vol. 25, No. 5.
Doerfler, P. A. et al. "Copackaged AAV9 Vectors Promote Simultaneous Immune Tolerance and Phenotypic Correction of Pompe Disease" *Human Gene Therapy*, Jan. 2016, pp. 43-59, vol. 27, No. 1.
Sun, B. et al. "Enhanced Efficacy of an AAV Vector Encoding Chimeric, Highly Secreted Acid α-Glucosidase in Glycogen Storage Disease Type II" *Molecular Therapy*, Dec. 2006, pp. 822-830, vol. 14, No. 6.
Database Geneseq [Online] Accession No. BAW43522, Dec. 5, 2013, XP-002767220, pp. 1-3.
Written Opinion in International Application No. PCT/EP2017/072942, dated Dec. 7, 2017, pp. 1-9.

* cited by examiner

*Primary Examiner* — Maryam Monshipouri
(74) *Attorney, Agent, or Firm* — Saliwanchik, Lloyd & Eisenschenk

(57) ABSTRACT

The present invention relates to variants of acid-alpha glucosidase and uses thereof. Said variants are sequence-optimized and/or are linked to a heterogenous signal peptide.

Figure 1:
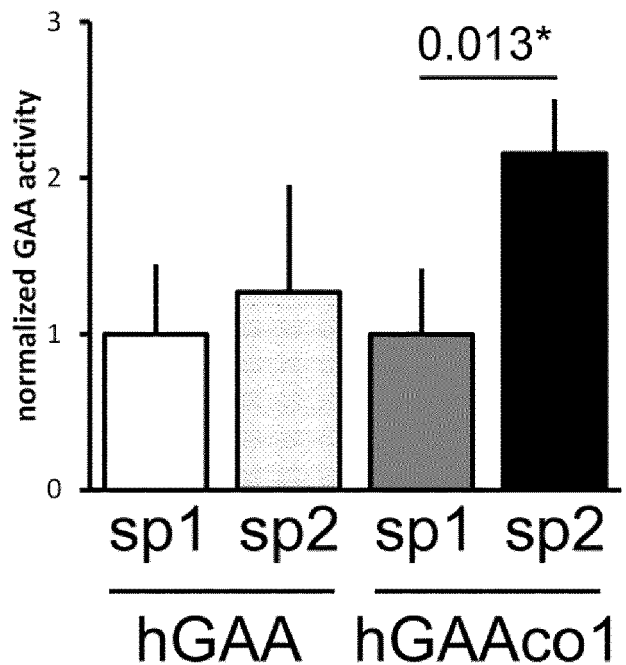

9 Claims, 1 Drawing Sheet
Specification includes a Sequence Listing.

SEQUENCE LISTING

<160> NUMBER OF SEQ ID NOS: 22

<210> SEQ ID NO 1
<211> LENGTH: 2778
<212> TYPE: DNA
<213> ORGANISM: artificial
<220> FEATURE:
<223> OTHER INFORMATION: hGAAco1 w/o sp

<400> SEQUENCE: 1

```
ggccatatcc tgctgcacga ctttctacta gtgcccagag agctgagcgg cagctctccc      60
gtgctggaag aaacacaccc tgcccatcag cagggcgcct ctagacctgg acctagagat     120
gcccaggccc accccggcag acctagagct gtgcctaccc agtgtgacgt gccccccaac     180
agcagattcg actgcgcccc tgacaaggcc atcacccagg aacagtgcga ggccagaggc     240
tgctgctaca tccctgccaa gcagggactg cagggcgctc agatgggaca gccctggtgc     300
ttcttcccac cctcctaccc cagctacaag ctggaaaacc tgagcagcag cgagatgggc     360
tacaccgcca ccctgaccag aaccaccccc acattcttcc caaggacat cctgaccctg     420 cggctggacg tgatgatgga aaccgagaac cggctgcact tcaccatcaa ggacccccgcc     480 aatcggagat acgaggtgcc cctggaaacc ccccacgtgc actctagagc ccccagccct     540
ctgtacagcg tggaattcag cgaggaaccc ttcggcgtga tcgtgcggag acagctggat     600
ggcagagtgc tgctgaacac caccgtggcc cctctgttct tcgccgacca gttcctgcag     660
ctgagcacca gcctgcccag ccagtacatc acaggactgg ccgagcacct gagccccctg     720
```

```
atgctgagca catcctggac ccggatcacc ctgtggaaca gggatctggc ccctacccct      780
ggcgccaatc tgtacggcag ccacccttc tacctggccc tggaagatgg cggatctgcc       840
cacggagtgt ttctgctgaa ctccaacgcc atggacgtgg tgctgcagcc tagccctgcc      900
ctgtcttgga aagcacagg cggcatcctg gatgtgtaca tctttctggg ccccgagccc       960
aagagcgtgg tgcagcagta tctggatgtc gtgggctacc ccttcatgcc cccttactgg     1020
ggcctgggat tccacctgtg cagatggggc tactccagca ccgccatcac cagacaggtg     1080
gtggaaaaca tgaccagagc ccacttccca ctggatgtgc agtggaacga cctggactac     1140
atggacagca cgggacttc accttcaac aaggacggct ccgggactt ccccgccatg        1200 gtgcaggaac tgcatcaggg cggcagacgg tacatgatga tcgtggatcc cgccatcagc     1260
tcctctggcc ctgccggctc ttacagaccc tacgacgagg gctgcgcgag aggcgtgttc     1320
atcaccaacg agacaggcca gcccctgatc ggcaaagtgt ggcctggcag cacagccttc     1380
cccgacttca ccaatcctac cgccctggct tggtgggagg acatggtggc cgagttccac     1440
gaccaggtgc ccttcgacgg catgtggatc gacatgaaca agcccagcaa cttcatccgg     1500
ggcagcgagg atggctgccc caacaacgaa ctggaaaatc cccttacgt gcccggcgtc      1560 gtgggcggaa cactgcaggc cgctacaatc tgtgccagca ccaccagtt tctgagcacc      1620 cactacaacc tgcacaacct gtacggcctg accgaggcca ttgccagcca ccgcgctctc     1680
gtgaaagcca aggcacacg gcccttcgtg atcagcagaa gcacctttgc cggccacggc     1740
agatacgccg acattggac tggcgacgtg tggtcctctt gggagcagct ggcctctagc     1800
gtgcccgaga tcctgcagtt caatctgctg gcgtgccac tcgtgggcgc cgatgtgtgt    1860
ggcttcctgg caacacctc cgaggaactg tgtgtgcggt ggacacagct gggcgccttc     1920
taccctttca tgagaaacca caacagcctg ctgagcctgc cccaggaacc ctacagcttt     1980
agcgagcctg cacagcaggc catgcggaag gccctgacac tgagatacgc tctgctgccc     2040
cacctgtaca ccctgtttca ccaggcccat gtggccggcg agacagtggc cagacctctg     2100
tttctggaat ccccaagga cagcagcacc tggaccgtgg accatcagct gctgtgggga     2160
gaggctctgc tgattacccc agtgctgcag gcaggcaagg ccgaagtgac cggctacttt     2220
cccctgggca cttggtacga cctgcagacc gtgcctgtgg aagccctggg atctctgcct     2280
ccacctcctg ccgctcctag agagcctgcc attcactctg agggccagtg ggtcacactg     2340
cctgcccccc tggataccat caacgtgcac ctgagggccg gctacatcat accactgcag     2400
ggacctggcc tgaccaccac cgagtctaga cagcagccaa tggccctggc cgtggccctg     2460
accaaaggcg agaagctag gggcgagctg ttctgggacg atggcgagag cctggaagtg     2520
ctggaaagag cgcctatac ccaagtgatc ttcctggccc cgaacaacac catcgtgaac     2580
gagctggtgc gcgtgacctc tgaaggcgct ggactgcagc tgcagaaagt gaccgtgctg     2640
ggagtggcca cagcccctca gcaggtgctg tctaatggcg tgcccgtgtc caacttcacc     2700
tacagccccg acaccaaggt gctggacatc tgcgtgtcac tgctgatggg agagcagttt     2760
ctggtgtcct ggtgctga                                                  2778

<210> SEQ ID NO 2
<211> LENGTH: 2778
<212> TYPE: DNA
<213> ORGANISM: artificial
<220> FEATURE:
<223> OTHER INFORMATION: hGAAco2 w/o sp

<400> SEQUENCE: 2
```

```
ggacacatcc tgctgcacga cttcctgttg gtgcctagag agctgagcgg atcatcccca    60
gtgctggagg agactcatcc tgctcaccaa cagggagctt ccagaccagg accgagagac   120
gcccaagccc atcctggtag accaagagct gtgcctaccc aatgcgacgt gccacccaac   180
tcccgattcg actgcgcgcc agataaggct attacccaag agcagtgtga agccagaggt   240
tgctgctaca tcccagcgaa gcaaggattg caaggcgccc aaatgggaca accttggtgt   300
ttcttccccc cttcgtaccc atcatataaa ctcgaaaacc tgtcctcttc ggaaatgggt   360
tatactgcca ccctcaccag aactactcct actttcttcc cgaaagacat cttgaccttg   420
aggctggacg tgatgatgga gactgaaaac cggctgcatt tcactatcaa agatcctgcc   480
aatcggcgat acgaggtccc tctggaaacc cctcacgtgc actcacgggc tccttctccg   540
ctttactccg tcgaattctc tgaggaaccc ttcggagtga tcgttagacg ccagctggat   600
ggtagagtgc tgttgaacac tactgtggcc ccacttttct tcgctgacca gtttctgcaa   660
ctgtccactt ccctgccatc ccagtacatt actggactcg ccgaacacct gtcgccactg   720
atgctctcga cctcttggac tagaatcact ttgtggaaca gagacttggc ccctactccg   780
ggagcaaatc tgtacggaag ccacccttt tacctggcgc tcgaagatgg cggatccgct    840
cacggagtgt tcctgctgaa tagcaacgca atggacgtgg tgctgcaacc ttcccctgca   900
ctcagttgga gaagtaccgg gggtattctg gacgtgtaca tcttcctcgg accagaaccc   960
aagagcgtgg tgcagcaata tctggacgtg gtcggatacc cttttatgcc tccttactgg  1020
ggactgggat ccaccttttg ccgttggggc tactcatcca ccgccattac agacaggtg   1080
gtggagaata tgaccagagc ccacttccct ctcgacgtgc agtggaacga tctggactat  1140
atggactccc ggagagattt caccttcaac aaggacgggt tccgcgattt tcccgcgatg  1200
gttcaagagc tccaccaggg tggtcgaaga tatatgatga tcgtcgaccc agccatttcg  1260
agcagcggac ccgctggatc ttatagacct tacgacgaag gccttaggag aggagtgttc  1320
atcacaaacg agactggaca gcctttgatc ggtaaagtgt ggcctggatc aaccgccttt  1380
cctgacttta ccaatcccac tgccttggct tggtgggagg acatggtggc cgaattccac  1440
gaccaagtcc cctttgatgg aatgtggatc gatatgaacg aaccaagcaa ttttatcaga  1500
ggttccgaag acggttgccc caacaacgaa ctggaaaacc ctccttatgt gcccggagtc  1560
gtgggcggaa cattacaggc cgcgactatt tgcgccagca gccaccaatt cctgtccact  1620
cactacaacc tccacaacct ttatggatta accgaagcta ttgcaagtca cagggctctg  1680
gtgaaggcta gagggactag gcccttttgtg atctcccgat ccaccttttgc cggacacggg  1740
agatacgccg gtcactggac tggtgacgtg tggagctcat gggaacaact ggcctcctcc  1800
gtgccggaaa tcttacagtt caaccttctg ggtgtccctc ttgtcggagc agacgtgtgt  1860
gggtttcttg gtaacaccct cgaggaactg tgtgtgcgct ggactcaact gggtgcattc  1920
tacccattca tgagaaacca caactccttg ctgtccctgc acaagagcc ctactcgttc   1980
agcgagcctg cacaacaggc tatgcggaag gcactgaccc tgagatacgc cctgcttcca  2040
cacttataca ctctcttcca tcaagcgcat gtggcaggag aaaccgttgc aaggcctctt  2100
ttccttgaat tccccaagga ttcctcgact tggacggtgg atcatcagct gctgtgggga  2160
gaagctctgc tgattactcc agtgttgcaa gccggaaaag ctgaggtgac cggatacttt  2220
ccgctgggaa cctggtacga cctccagact gtccctgttg aagcccttgg atcactgcct  2280
ccgcctccgg cagctccacg cgaaccagct atacattccg agggacagtg ggttacatta  2340
```

```
ccagctcctc tggacacaat caacgtccac ttaagagctg gctacattat ccctctgcaa    2400
ggaccaggac tgactacgac cgagagcaga cagcagccaa tggcactggc tgtggctctg    2460
accaagggag gggaagctag aggagaactc ttctgggatg atggggagtc ccttgaagtg    2520
ctggaaagag gcgcttacac tcaagtcatt ttccttgcac ggaacaacac cattgtgaac    2580
gaattggtgc gagtgaccag cgaaggagct ggacttcaac tgcagaaggt cactgtgctc    2640
ggagtggcta ccgctcctca gcaagtgctg tcgaatggag tccccgtgtc aaactttacc    2700
tactcccctg acactaaggt gctcgacatt tgcgtgtccc tcctgatggg agagcagttc    2760
cttgtgtcct ggtgttga                                                 2778

<210> SEQ ID NO 3
<211> LENGTH: 2859
<212> TYPE: DNA
<213> ORGANISM: artificial
<220> FEATURE:
<223> OTHER INFORMATION: hGAAwt w/ sp1

<400> SEQUENCE: 3
atgggagtga ggcacccgcc ctgctcccac cggctcctgg ccgtctgcgc cctcgtgtcc    60
ttggcaaccg ctgcactcct ggggcacatc ctactccatg atttcctgct ggttccccga    120
gagctgagtg gctcctcccc agtcctggag gagactcacc cagctcacca gcaggagcc    180 agcagaccag gccccgggga tgcccaggca caccccggcc gtcccagagc agtgcccaca    240
cagtgcgacg tccccccaa cagccgcttc gattgcgccc tgacaaggc catcacccag    300 gaacagtgcg aggcccgcgg ctgctgctac atccctgcaa agcaggggct gcagggagcc    360
cagatggggc agccctggtg cttcttccca cccagctacc cagctacaa gctggagaac    420 ctgagctcct ctgaaatggg ctacacggcc accctgaccc gtaccacccc caccttcttc    480
cccaaggaca tcctgacct gcggctggac gtgatgatgg agactgagaa ccgcctccac    540
ttcacgatca agatccagc taacaggcgc tacgaggtgc ccttggagac cccgcgtgtc    600
cacagccggg caccgtcccc actctacagc gtggagttct ccgaggagcc cttcggggtg    660
atcgtgcacc ggcagctgga cggccgcgtg ctgctgaaca cgacggtggc gcccctgttc    720
tttgcggacc agttccttca gctgtccacc tcgctgccct cgcagtatat cacaggcctc    780
gccgagcacc tcagtcccct gatgctcagc accagctgga ccaggatcac cctgtggaac    840
cgggaccttg cgccacgcc cggtgcgaac ctctacgggt ctcaccctt ctacctggcg    900 ctggaggacg gcgggtcggc cacggggtg ttcctgctaa acagcaatgc catggatgtg    960
gtcctgcagc cgagccctgc ccttagctgg aggtcgacag gtgggatcct ggatgtctac    1020
atcttcctgg gccagagcc caagagcgtg gtgcagcagt acctggacgt tgtgggatac    1080
ccgttcatgc cgccatactg gggcctgggc ttccacctgt gccgctgggg ctactcctcc    1140
accgctatca cccgccaggt ggtggagaac atgaccaggg cccacttccc cctggacgtc    1200
caatggaacg acctggacta catggactcc cggagggact tcacgttcaa caaggatggc    1260
ttccgggact ccccggccat ggtgcaggag ctgcaccagg gcggccggcg ctacatgatg    1320
atcgtggatc ctgccatcag cagctcgggc cctgccggga gctacaggcc ctacgacgag    1380
ggtctgcgga gggggggttttt catcaccaac gagaccggcc agccgctgat tgggaaggta    1440
tggcccgggt ccactgcctt ccccgacttc accaacccca cagccctggc ctggtgggag    1500
gacatggtgc ctgagttcca tgaccaggtg cccttcgacg gcatgtggat tgacatgaac    1560
gagccttcca acttcatcag aggctctgag gacggctgcc ccaacaatga gctggagaac    1620
```

```
ccaccctacg tgcctggggt ggttgggggg accctccagg cggccaccat ctgtgcctcc    1680
agccaccagt ttctctccac acactacaac ctgcacaacc tctacggcct gaccgaagcc    1740
atcgcctccc acagggcgct ggtgaaggct cgggggacac gcccatttgt gatctcccgc    1800
tcgacctttg ctggccacgg ccgatacgcc ggccactgga cggggacgt gtggagctcc     1860 tgggagcagc tcgcctcctc cgtgccagaa atcctgcagt ttaacctgct ggggtgcct     1920 ctggtcgggg ccgacgtctg cggcttcctg ggcaacacct cagaggagct gtgtgtgcgc    1980
tggacccagc tgggggcctt ctaccccttc atgcggaacc acaacagcct gctcagtctg    2040
ccccaggagc cgtacagctt cagcgagccg gcccagcagg ccatgaggaa ggccctcacc    2100
ctgcgctacg cactcctccc ccacctctac acactgttcc accaggccca cgtcgcgggg    2160
gagaccgtgg cccggcccct cttcctggag ttccccaagg actctagcac ctggactgtg    2220
gaccaccagc tcctgtgggg ggaggccctg ctcatcaccc cagtgctcca ggccgggaag    2280
gccgaagtga ctggctactt cccttgggc acatggtacg acctgcagac ggtgccaata     2340
gaggcccttg gcagcctccc accccacct gcagctcccc gtgagccagc catccacagc     2400 gagggggcagt gggtgacgct gccggccccc ctggacacca tcaacgtcca cctccgggct    2460
gggtacatca tccccctgca gggccctggc ctcacaacca cagagtcccg ccagcagccc    2520
atggccctgg ctgtggccct gaccaagggt ggagaggccc gagggagct gttctgggac     2580 gatggagaga gcctggaagt gctggagcga ggggcctaca caccggtcat cttcctggcc    2640
aggaataaca cgatcgtgaa tgagctggta cgtgtgacca gtgagggagc tggcctgcag    2700
ctgcagaagg tgactgtcct gggcgtggcc acggcgcccc agcaggtcct ctccaacggt    2760
gtccctgtct ccaacttcac ctacagcccc gacaccaagg tcctggacat ctgtgtctcg    2820
ctgttgatgg gagagcagtt tctcgtcagc tggtgttag                          2859
```

<210> SEQ ID NO 4
<211> LENGTH: 24
<212> TYPE: PRT
<213> ORGANISM: artificial
<220> FEATURE:
<223> OTHER INFORMATION: sp2

<400> SEQUENCE: 4

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 5
<211> LENGTH: 397
<212> TYPE: DNA
<213> ORGANISM: artificial
<220> FEATURE:
<223> OTHER INFORMATION: hAAT promoter

<400> SEQUENCE: 5

```
gatcttgcta ccagtggaac agccactaag gattctgcag tgagagcaga gggccagcta     60
agtggtactc tcccagagac tgtctgactc acgccacccc ctccaccttg gacacaggac    120
gctgtggttt ctgagccagg tacaatgact cctttcggta agtgcagtgg aagctgtaca    180
ctgcccaggc aaagcgtccg ggcagcgtag gcgggcgact cagatcccag ccagtggact    240 tagccccgt ttgctcctcc gataactggg gtgaccttgg ttaatattca ccagcagcct    300
```

```
ccccgttgc ccctctggat ccactgctta aatacggacg aggacagggc cctgtctcct    360
cagcttcagg caccaccact gacctgggac agtgaat                             397

<210> SEQ ID NO 6
<211> LENGTH: 321
<212> TYPE: DNA
<213> ORGANISM: artificial
<220> FEATURE:
<223> OTHER INFORMATION: ApoE control region

<400> SEQUENCE: 6
aggctcagag gcacacagga gtttctgggc tcaccctgcc ccttccaac ccctcagttc     60 ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctggggcaga ggtcagagac ctctctgggc ccatgccacc   240
tccaacatcc actcgacccc ttggaatttc ggtggagagg agcagaggtt gtcctggcgt   300
ggtttaggta gtgtgagagg g                                              321

<210> SEQ ID NO 7
<211> LENGTH: 441
<212> TYPE: DNA
<213> ORGANISM: artificial
<220> FEATURE:
<223> OTHER INFORMATION: HBB2 intron

<400> SEQUENCE: 7
gtacacatat tgaccaaatc agggtaattt tgcatttgta attttaaaaa atgctttctt    60
cttttaatat actttttgt ttatcttatt tctaatactt tccctaatct ctttctttca   120
gggcaataat gatacaatgt atcatgcctc tttgcaccat tctaaagaat aacagtgata   180
atttctgggt taaggcaata gcaatatttc tgcatataaa tatttctgca tataaattgt   240
aactgatgta agaggtttca tattgctaat agcagctaca atccagctac cattctgctt   300 ttatttatg gttgggataa ggctggatta ttctgagtcc aagctaggcc ttttgctaa    360 tcatgttcat acctcttatc ttcctcccac agctcctggg caacgtgctg gtctgtgtgc   420
tggcccatca ctttggcaaa g                                              441

<210> SEQ ID NO 8
<211> LENGTH: 441
<212> TYPE: DNA
<213> ORGANISM: artificial
<220> FEATURE:
<223> OTHER INFORMATION: modified HBB2 intron

<400> SEQUENCE: 8
gtacacatat tgaccaaatc agggtaattt tgcatttgta attttaaaaa atgctttctt    60
cttttaatat actttttgt ttatcttatt tctaatactt tccctaatct ctttctttca   120
gggcaataat gatacaatgt atcatgcctc tttgcaccat tctaaagaat aacagtgata   180
atttctgggt taaggcaata gcaatatttc tgcatataaa tatttctgca tataaattgt   240
aactgatgta agaggtttca tattgctaat agcagctaca atccagctac cattctgctt   300
ttattttctg gttgggataa ggctggatta ttctgagtcc aagctaggcc ttttgctaa   360 tcttgttcat acctcttatc ttcctcccac agctcctggg caacctgctg gtctctctgc   420
tggcccatca ctttggcaaa g                                              441
```

```
<210> SEQ ID NO 9
<211> LENGTH: 1438
<212> TYPE: DNA
<213> ORGANISM: artificial
<220> FEATURE:
<223> OTHER INFORMATION: FIX intron

<400> SEQUENCE: 9
ggtttgtttc cttttttaaa atacattgag tatgcttgcc ttttagatat agaaatatct      60
gatgctgtct tcttcactaa attttgatta catgatttga cagcaatatt gaagagtcta     120
acagccagca cgcaggttgg taagtactgg ttctttgtta gctaggtttt cttcttcttc     180 attttttaaaa ctaaatagat cgacaatgct tatgatgcat ttatgtttaa taaacactgt     240
tcagttcatg atttggtcat gtaattcctg ttagaaaaca ttcatctcct tggtttaaaa     300
aaattaaaag tgggaaaaca agaaatagc agaatatagt gaaaaaaaat aaccacatta     360
tttttgtttg gacttaccac tttgaaatca aaatgggaaa caaaagcaca acaatggcc     420 ttatttacac aaaaagtctg attttaagat atatgacatt tcaaggtttc agaagtatgt     480
aatgaggtgt gtctctaatt ttttaaatta tatatcttca atttaaagtt ttagttaaaa     540
cataaagatt aacctttcat tagcaagctg ttagttatca ccaacgcttt tcatggatta     600
ggaaaaaatc attttgtctc tatgtcaaac atcttggagt tgatatttgg ggaaacacaa     660
tactcagttg agttccctag gggagaaaag cacgcttaag aattgacata agagtagga     720 agttagctaa tgcaacatat atcactttgt tttttcacaa ctacagtgac tttatgtatt     780
tcccagagga aggcatacag ggaagaaatt atcccatttg gacaaacagc atgttctcac     840
aggaagcatt tatcacactt acttgtcaac tttctagaat caaatctagt agctgacagt     900
accaggatca ggggtgccaa ccctaagcac ccccagaaag ctgactggcc ctgtggttcc     960
cactccagac atgatgtcag ctgtgaaatc gacgtcgctg gaccataatt aggcttctgt    1020
tcttcaggag acatttgttc aaagtcattt gggcaaccat attctgaaaa cagcccagcc    1080
agggtgatgg atcactttgc aaagatcctc aatgagctat tttcaagtga tgacaaagtg    1140
tgaagttaac cgctcatttg agaactttct ttttcatcca agtaaattc aaatatgatt    1200 agaaatctga cctttattta ctggaattct cttgactaaa agtaaaattg aattttaatt    1260
cctaaatctc catgtgtata cagtactgtg ggaacatcac agattttggc tccatgccct    1320
aaagagaaat tggcttcag attatttgga ttaaaaacaa agactttctt aagagatgta    1380 aaatttttcat gatgttttct tttttgctaa aactaaagaa ttattctttt acatttca    1438

<210> SEQ ID NO 10
<211> LENGTH: 1438
<212> TYPE: DNA
<213> ORGANISM: artificial
<220> FEATURE:
<223> OTHER INFORMATION: modified FIX intron

<400> SEQUENCE: 10
ggtttgtttc cttttttaaa atacattgag tatgcttgcc ttttagatat agaaatatct      60
gatgctgtct tcttcactaa attttgatta catgatttga cagcaatatt gaagagtcta     120
acagccagca cgcaggttgg taagtactgg ttctttgtta gctaggtttt cttcttcttc     180 attttttaaaa ctaaatagat cgacattgct tttgttgcat ttatgtttaa taaacactgt     240
tcagttcatg atttggtcat gtaattcctg ttagaaaaca ttcatctcct tggtttaaaa     300
aaattaaaag tgggaaaaca agaaatagc agaatatagt gaaaaaaaat aaccacatta     360
```

-continued

| | |
|---|---|
| ttttttgtttg gacttaccac tttgaaatca aattgggaaa caaaagcaca aacaatggcc | 420 |
| ttatttacac aaaaagtctg attttaagat atatgacatt tcaaggtttc agaagtatgt | 480 |
| aatgaggtgt gtctctaatt ttttaaatta tatatcttca atttaaagtt ttagttaaaa | 540 |
| cataaagatt aacctttcat tagcaagctg ttagttatca ccaacgcttt tcatggatta | 600 |
| ggaaaaaatc attttgtctc tttgtcaaac atcttggagt tgatatttgg ggaaacacaa | 660 |
| tactcagttg agttccctag gggagaaaag cacgcttaag aattgacata aagagtagga | 720 |
| agttagctat tgcaacatat atcactttgt tttttcacaa ctacagtgac ttttttgtatt | 780 |
| tcccagagga aggcatacag ggaagaaatt atcccatttg acaaacagc ttgttctcac | 840 |
| aggaagcatt tatcacactt acttgtcaac tttctagaat caaatctagt agctgacagt | 900 |
| accaggatca ggggtgccaa ccctaagcac ccccagaaag ctgactggcc ctgtggttcc | 960 |
| cactccagac atgatgtcag ctgtgaaatc gacgtcgctg gaccataatt aggcttctgt | 1020 |
| tcttcaggag acatttgttc aaagtcattt gggcaaccat attctgaaaa cagcccagcc | 1080 |
| agggtgttgg atcactttgc aaagatcctc attgagctat tttcaagtgt tgacaaagtg | 1140 |
| tgaagttaac cgctcatttg agaactttct ttttcatcca agtaaattc aaatatgatt | 1200 |
| agaaatctga cctttattta ctggaattct cttgactaaa agtaaaattg aattttaatt | 1260 |
| cctaaatctc catgtgtata cagtactgtg ggaacatcac agattttggc tccatgccct | 1320 |
| aaagagaaat tggcttcag attatttgga ttaaaaacaa agactttctt aagagatgta | 1380 |
| aaattttctt gttgttttct tttttgctaa aactaaagaa ttattctttt acatttca | 1438 |

<210> SEQ ID NO 11
<211> LENGTH: 881
<212> TYPE: DNA
<213> ORGANISM: artificial
<220> FEATURE:
<223> OTHER INFORMATION: chicken beta-globin intron

<400> SEQUENCE: 11

| | |
|---|---|
| gcgggagtcg ctgcgttgcc ttcgccccgt gccccgctcc gccgccgcct cgcgccgccc | 60 |
| gccccggctc tgactgaccg cgttactccc acaggtgagc gggcgggacg gcccttctcc | 120 |
| tccgggctgt aattagcgct tggtttaatg acggcttgtt tcttttctgt ggctgcgtga | 180 |
| aagccttgag gggctccggg agggcccttt gtgcgggggg agcggctcgg ggggtgcgtg | 240 |
| cgtgtgtgtg tgcgtgggga cgccgcgtg cggctccgcg ctgcccggcg gctgtgagcg | 300 |
| ctgcgggcgc ggcgcggggc tttgtgcgct ccgcagtgtg cgcgagggga gcgcggccgg | 360 |
| gggcggtgcc ccgcggtgcg gggggggctg cgaggggaac aaaggctgcg tgcggggtgt | 420 |
| gtgcgtgggg gggtgagcag ggggtgtggg cgcgtcggtc gggctgcaac ccccctgca | 480 |
| cccccctccc cgagttgctg agcacggccc ggcttcgggt gcgggctcc gtacggggcg | 540 |
| tggcgcgggg ctcgccgtgc cgggcggggg gtggcggcag gtgggggtgc cgggcggggc | 600 |
| ggggccgcct cggccgggg agggctcggg ggaggggcgc ggcggccccc ggagcgccgg | 660 |
| cggctgtcga ggcgcggcga gccgcagcca ttgccttta tggtaatcgt gcgagagggc | 720 |
| gcagggactt cctttgtccc aaatctgtgc ggagccgaaa tctgggaggc gccgccgcac | 780 |
| cccctctagc gggcgcgggg cgaagcggtg cggcgccggc aggaaggaaa tgggcgggga | 840 |
| gggccttcgt gcgtcgccgc gccgccgtcc ccttctccct c | 881 |

<210> SEQ ID NO 12
<211> LENGTH: 881

```
<212> TYPE: DNA
<213> ORGANISM: artificial
<220> FEATURE:
<223> OTHER INFORMATION: modified chicken beta-globin intron

<400> SEQUENCE: 12
gcgggagtcg ctgcgttgcc ttcgccccgt gccccgctcc gccgccgcct cgcgccgccc    60
gccccggctc tgactgaccg cgttactccc acaggtgagc gggcgggacg gcccttctcc   120
tccgggctgt aattagcgct tggtttaatg acggcttgtt tcttttctgt ggctgcgtga   180
aagccttgag gggctccggg agggcccttt gtgcgggggg agcggctcgg ggggtgcgtg   240
cgtgtgtgtg tgcgtgggga gcgccgcgtg cggctccgcg ctgcccggcg ctgtgagcg    300 ctgcgggcgc ggcgcggggc tttgtgcgct ccgcagtgtg cgcgagggga gcgcggccgg   360
gggcggtgcc ccgcggtgcg ggggggctg cgagggaac aaaggctgcg tgcgggtgt     420 gtgcgtgggg gggtgagcag ggggtgtggg cgcgtcggtc gggctgcaac ccccctgca   480 ccccctccc cgagttgctg agcacggcc ggcttcgggt gcggggctcc gtacggggcg    540
tggcgcgggg ctcgccgtgc cgggcggggg gtggcggcag gtggggtgc cgggcggggc   600 ggggccgcct cgggccgggg agggctcggg ggaggggcgc ggcggccccc ggagcgccgg   660
cggctgtcga ggcgcggcga gccgcagcca ttgcctttttt tggtaatcgt gcgagagggc   720
gcagggactt cctttgtccc aaatctgtgc ggagccgaaa tctgggaggc gccgccgcac   780
cccctctagc gggcgcgggg cgaagcggtg cggcgccggc aggaaggaat tgggcgggga   840
gggccttcgt gcgtcgccgc gccgccgtcc ccttctccct c                      881

<210> SEQ ID NO 13
<211> LENGTH: 4342
<212> TYPE: DNA
<213> ORGANISM: artificial
<220> FEATURE:
<223> OTHER INFORMATION: expression cassette including sp2/hGAAco1

<400> SEQUENCE: 13
aggctcagag gcacacagga gtttctgggc tcaccctgcc cccttccaac ccctcagttc    60
ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctggggcaga ggtcagagac ctctctgggc ccatgccacc   240
tccaacatcc actcgacccc ttggaatttc ggtggagagg agcagaggtt gtcctggcgt   300
ggtttaggta gtgtgagagg ggtacccggg gatcttgcta ccagtggaac agccactaag   360
gattctgcag tgagagcaga gggccagcta agtggtactc tcccagagac tgtctgactc   420
acgccacccc ctccaccttg gacacaggac gctgtggttt ctgagccagg tacaatgact   480
cctttcggta agtgcagtgg aagctgtaca ctgcccaggc aaagcgtccg ggcagcgtag   540
gcgggcgact cagatcccag ccagtggact tagcccctgt ttgctcctcc gataactggg   600
gtgaccttgg ttaatattca ccagcagcct cccccgttgc ccctctggat ccactgctta   660 aatacgacg aggacagggc cctgtctcct cagcttcagg caccaccact gacctgggac   720
agtgaataga tcctgagaac ttcagggtga gtctatggga cccttgatgt tttctttccc   780
cttcttttct atggttaagt tcatgtcata ggaagggggg agt aacagg gtacacatat   840 tgaccaaatc agggtaattt tgcatttgta atttttaaaaa atgctttctt cttttaatat   900
acttttttgt ttatcttatt tctaatactt tccctaatct cttctcttca gggcaataat   960
```

```
gatacaatgt atcatgcctc tttgcaccat tctaaagaat aacagtgata atttctgggt    1020
taaggcaata gcaatatttc tgcatataaa tatttctgca tataaattgt aactgatgta    1080
agaggtttca tattgctaat agcagctaca atccagctac cattctgctt ttattttctg    1140
gttgggataa ggctggatta ttctgagtcc aagctaggcc cttttgctaa tcttgttcat    1200
acctcttatc ttcctcccac agctcctggg caacctgctg gtctctctgc tggcccatca    1260
ctttggcaaa gcacgcgtgc caccatgcct agctctgtgt cctggggcat tctgctgctg    1320
gccggcctgt gttgtctggt gcctgtgtct ctggccggcc atatcctgct gcacgacttt    1380
ctactagtgc ccagagagct gagcggcagc tctcccgtgc tggaagaaac acaccctgcc    1440
catcagcagg gcgcctctag acctggacct agagatgccc aggcccaccc cggcagacct    1500
agagctgtgc ctacccagtg tgacgtgccc cccaacagca gattcgactg cgcccctgac    1560
aaggccatca cccaggaaca gtgcgaggcc agaggctgct gctacatccc tgccaagcag    1620
ggactgcagg gcgctcagat gggacagccc tggtgcttct tcccacccct ctaccccagc    1680
tacaagctgg aaaacctgag cagcagcgag atgggctaca ccgccaccct gaccagaacc    1740
acccccacat tcttcccaaa ggacatcctg accctgcggc tggacgtgat gatggaaacc    1800
gagaaccggc tgcacttcac catcaaggac cccgccaatc ggagatacga ggtgcccctg    1860
gaaacccccc acgtgcactc tagagccccc agccctctgt acagcgtgga attcagcgag    1920
gaaccctccg gcgtgatcgt gcggagacag ctggatggca gagtgctgct gaacaccacc    1980
gtggcccctc tgttcttcgc cgaccagttc ctgcagctga gcaccagcct gcccagccag    2040
tacatcacag gactggccga gcacctgagc cccctgatgc tgagcacatc ctggaccggg    2100
atcaccctgt ggaacaggga tctggcccct accctggcg ccaatctgta cggcagccac    2160 ccttctacc tggccctgga agatggcgga tctgcccacg gagtgttcct gctgaactcc    2220
aacgccatgg acgtggtgct gcagcctagc cctgccctgt cttggagaag cacaggcggc    2280
atcctggatg tgtacatctt tctgggcccc gagcccaaga gcgtggtgca gcagtatctg    2340
gatgtcgtgg gctaccccct catgcccccct tactgggcc tgggattcca cctgtgcaga    2400
tggggctact ccagcaccgc catcaccaga caggtggtgg aaaacatgac cagagcccac    2460
ttcccactgg atgtgcagtg gaacgacctg gactacatgg acagcagacg ggacttcacc    2520
ttcaacaagg acggcttccg ggacttcccc gccatggtgc aggaactgca tcagggcggc    2580
agacggtaca tgatgatcgt ggatcccgcc atcagctcct ctggccctgc cggctcttac    2640
agaccctacg acgagggcct gcggagaggc gtgttcatca ccaacgagac aggccagccc    2700
ctgatcggca aagtgtggcc tggcagcaca gccttccccg acttcaccaa tcctaccgcc    2760
ctggcttggt gggaggacat ggtggccgag ttccacgacc aggtgccctt cgacggcatg    2820
tggatcgaca tgaacgagcc cagcaacttc atccgggca gcgaggatgg ctgccccaac    2880
aacgaactgg aaaatccccc ttacgtgccc ggcgtcgtgg gcggaacact gcaggccgct    2940
acaatctgtg ccagcagcca ccagtttctg agcacccact acaacctgca caacctgtac    3000
ggcctgaccg aggccattgc cagccaccgc gctctcgtga agccagagg cacacggccc    3060 ttcgtgatca gcagaagcac cttgccggc cacggcagat acgccggaca ttggactggc    3120
gacgtgtggt cctcttggga gcagctggcc tctagcgtgc ccgagatcct gcagttcaat    3180
ctgctgggcg tgccactcgt gggcgccgat gtgtgtggct tcctgggcaa cacctccgag    3240
gaactgtgtg tgcggtggac acagctgggc gccttctacc ctttcatgag aaaccacaac    3300
agcctgctga gcctgccccca ggaaccctac agctttagcg agcctgcaca gcaggccatg    3360
```

```
cggaaggccc tgacactgag atacgctctg ctgccccacc tgtacaccct gtttcaccag   3420
gcccatgtgg ccggcgagac agtggccaga cctctgtttc tggaattccc caaggacagc   3480
agcacctgga ccgtggacca tcagctgctg tggggagagg ctctgctgat taccccagtg   3540
ctgcaggcag gcaaggccga agtgaccggc tactttcccc tgggcacttg gtacgacctg   3600
cagaccgtgc ctgtggaagc cctgggatct ctgcctccac ctcctgccgc tcctagagag   3660
cctgccattc actctgaggg ccagtgggtc acactgcctg ccccctgga taccatcaac   3720 gtgcacctga gggccggcta catcatacca ctgcagggac ctggcctgac caccaccgag   3780
tctagacagc agccaatggc cctggccgtg ccctgacca aggcggaga agctagggc     3840 gagctgttct gggacgatgg cgagagcctg gaagtgctgg aaagaggcgc ctatacccaa   3900
gtgatcttcc tggcccggaa caacaccatc gtgaacgagc tggtgcgcgt gacctctgaa   3960
ggcgctggac tgcagctgca gaaagtgacc gtgctgggag tggccacagc ccctcagcag   4020
gtgctgtcta tggcgtgcc cgtgtccaac ttcacctaca gccccgacac caaggtgctg   4080
gacatctgcg tgtcactgct gatgggagag cagtttctgg tgtcctggtg ctgactcgag   4140
agatctaccg tgaattcac cgcgggttta aactgtgcct tctagttgcc agccatctgt   4200
tgtttgcccc tcccccgtgc cttccttgac cctggaaggt gccactccca ctgtcctttc   4260
ctaataaaat gaggaaattg catcgcattg tctgagtagg tgtcattcta ttctgggggg   4320
tggggtgggg gctagctcta ga                                           4342
```

<210> SEQ ID NO 14  
<211> LENGTH: 4342  
<212> TYPE: DNA  
<213> ORGANISM: artificial  
<220> FEATURE:  
<223> OTHER INFORMATION: expression cassette including sp2/hGAAco2

<400> SEQUENCE: 14

```
aggctcagag gcacacagga gtttctgggc tcaccctgcc cccttccaac ccctcagttc     60
ccatcctcca gcagctgttt gtgtgctgcc tctgaagtcc acactgaaca aacttcagcc    120
tactcatgtc cctaaaatgg gcaaacattg caagcagcaa acagcaaaca cacagccctc    180
cctgcctgct gaccttggag ctggggcaga ggtcagagac ctctctgggc ccatgccacc    240
tccaacatcc actcgacccc ttggaatttc ggtggagagg agcagaggtt gtcctggcgt    300
ggtttaggta gtgtgagagg ggtacccggg gatcttgcta ccagtggaac agccactaag    360
gattctgcag tgagagcaga gggccagcta agtggtactc tcccagagac tgtctgactc    420
acgccacccc ctccaccttg gacacaggac gctgtggttt ctgagccagg tacaatgact    480
cctttcggta agtgcagtgg aagctgtaca ctgcccaggc aaagcgtccg ggcagcgtag    540
gcgggcgact cagatcccag ccagtggact tagcccctgt tgctcctcc gataactggg     600 gtgaccttgg ttaatattca ccagcagcct ccccgttgc ccctctggat ccactgctta     660
aatacggacg aggacagggc cctgtctcct cagcttcagg caccaccact gacctgggac    720
agtgaataga tcctgagaac ttcagggtga gtctatggga cccttgatgt tttctttccc    780 cttctttttct atggttaagt tcatgtcata ggaaggggag aagtaacagg gtacacatat    840
tgaccaaatc agggtaattt tgcatttgta atttttaaaaa atgctttctt cttttaatat    900 actttttttgt ttatcttatt tctaatactt tccctaatct cttctcttttca gggcaataat    960 gatacaatgt atcatgcctc tttgcaccat tctaaagaat aacagtgata atttctgggt   1020
```

```
taaggcaata gcaatatttc tgcatataaa tatttctgca tataaattgt aactgatgta      1080
agaggtttca tattgctaat agcagctaca atccagctac cattctgctt ttattttctg      1140
gttgggataa ggctggatta ttctgagtcc aagctaggcc cttttgctaa tcttgttcat      1200
acctcttatc ttcctcccac agctcctggg caacctgctg gtctctctgc tggcccatca      1260
ctttggcaaa gcacgcgtgc caccatgcca tcgtcagtgt cttggggcat tcttctgctc      1320
gccggattgt gttgcctggt gcctgtctca ttggccggac acatcctgct gcacgacttc      1380
ctgttggtgc ctagagagct gagcggatca tccccagtgc tggaggagac tcatcctgct      1440
caccaacagg gagcttccag accaggaccg agagacgccc aagcccatcc tggtagacca      1500
agagctgtgc ctacccaatg cgacgtgcca cccaactccc gattcgactg cgcgccagat      1560
aaggctatta cccaagagca gtgtgaagcc agaggttgct gctacatccc agcgaagcaa      1620
ggattgcaag gcgcccaaat gggacaacct tggtgtttct tcccccccttc gtacccatca      1680 tataaactcg aaaacctgtc ctcttcggaa atgggttata ctgccaccct caccagaact      1740
actcctactt tcttcccgaa agacatcttg accttgaggc tggacgtgat gatggagact      1800
gaaaaccggc tgcatttcac tatcaaagat cctgccaatc ggcgatacga ggtccctctg      1860
gaaacccctc acgtgcactc acgggctcct tctccgcttt actccgtcga attctctgag      1920
gaacccttcg gagtgatcgt tagacgccag ctggatggta gagtgctgtt gaacactact      1980
gtggccccac ttttcttcgc tgaccagttt ctgcaactgt ccacttccct gccatcccag      2040
tacattactg gactcgccga cacctgtcg ccactgatgc tctcgacctc ttggactaga      2100
atcactttgt ggaacagaga cttggcccct actccgggag caaatctgta cggaagccac      2160
cctttttacc tggcgctcga agatggcgga tccgctcacg gagtgttcct gctgaatagc      2220
aacgcaatgg acgtggtgct gcaaccttcc cctgcactca gttggagaag taccgggggt      2280
attctggacg tgtacatctt cctcggacca gaacccaaga gcgtggtgca gcaatatctg      2340
gacgtggtcg gataccctt tatgcctcct tactggggac tgggattcca cctttgccgt      2400
tggggctact catccaccgc cattaccaga caggtggtgg agaatatgac cagagcccac      2460
ttccctctcg acgtgcagtg gaacgatctg gactatatgg actcccggag agatttcacc      2520
ttcaacaagg acgggttccg cgatttccc gcgatggttc aagagctcca ccagggtggt      2580
cgaagatata tgatgatcgt cgacccagcc atttcgagca gcggacccgc tggatcttat      2640
agaccttacg acgaaggcct taggagagga gtgttcatca caaacgagac tggacagcct      2700
ttgatcggta aagtgtggcc tggatcaacc gcctttcctg actttaccaa tcccactgcc      2760
ttggcttggt gggaggacat ggtggccgaa ttccacgacc aagtcccctt tgatggaatg      2820
tggatcgata tgaacgaacc aagcaatttt atcagaggtt ccgaagacgg ttgccccaac      2880
aacgaactgg aaaaccctcc ttatgtgccc ggagtcgtgg gcggaacatt acaggccgcg      2940
actatttgcg ccagcagcca ccaattcctg tccactcact acaacctcca caacctttat      3000
ggattaaccg aagctattgc aagtcacagg gctctggtga aggctagagg gactaggccc      3060
tttgtgatct cccgatccac ctttgccgga cacgggagat acgccggtca ctggactggt      3120
gacgtgtgga gctcatggga acaactggcc tcctccgtgc cggaaatctt acagttcaac      3180
cttctgggtg tccctcttgt cggagcagac gtgtgtgggt ttcttggtaa cacctccgag      3240
gaactgtgtg tgcgctggac tcaactgggt gcattctacc cattcatgag aaaccacaac      3300
tccttgctgt ccctgccaca agagcccta c tcgttcagcg agcctgcaca acaggctatg      3360
cggaaggcac tgacccctgag atacgccctg cttccacact tatacactct cttccatcaa      3420
```

-continued

```
gcgcatgtgg caggagaaac cgttgcaagg cctctttttcc ttgaattccc caaggattcc    3480
tcgacttgga cggtggatca tcagctgctg tggggagaag ctctgctgat tactccagtg    3540
ttgcaagccg aaaagctga ggtgaccgga tactttccgc tgggaacctg gtacgacctc    3600
cagactgtcc ctgttgaagc ccttggatca ctgcctccgc ctccggcagc tccacgcgaa    3660
ccagctatac attccgaggg acagtgggtt acattaccag ctcctctgga cacaatcaac    3720
gtccacttaa gagctggcta cattatccct ctgcaaggac caggactgac tacgaccgag    3780
agcagacagc agccaatggc actggctgtg gctctgacca agggagggga agctagagga    3840
gaactcttct gggatgatgg ggagtccctt gaagtgctgg aaagaggcgc ttacactcaa    3900
gtcattttcc ttgcacggaa caacaccatt gtgaacgaat ggtgcgagt gaccagcgaa    3960
ggagctggac ttcaactgca gaaggtcact gtgctcggag tggctaccgc tcctcagcaa    4020
gtgctgtcga atggagtccc cgtgtcaaac tttacctact cccctgacac taaggtgctc    4080
gacatttgcg tgtccctcct gatgggagag cagttccttg tgtcctggtg ttgactcgag    4140
agatctaccg gtgaattcac cgcgggttta aactgtgcct tctagttgcc agccatctgt    4200
tgtttgcccc tccccccgtgc cttccttgac cctggaaggt gccactccca ctgtcctttc    4260
ctaataaaat gaggaaattg catcgcattg tctgagtagg tgtcattcta ttctgggggg    4320
tggggtgggg gctagctcta ga                                              4342
```

<210> SEQ ID NO 15
<211> LENGTH: 925
<212> TYPE: PRT
<213> ORGANISM: artificial
<220> FEATURE:
<223> OTHER INFORMATION: hGAAwt w/o sp1

<400> SEQUENCE: 15

```
Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
    50                  55                  60

Cys Ala Pro Asp Lys Ala Ile Thr Gln Glu Gln Cys Glu Ala Arg Gly
65                  70                  75                  80

Cys Cys Tyr Ile Pro Ala Lys Gln Gly Leu Gln Gly Ala Gln Met Gly
                85                  90                  95

Gln Pro Trp Cys Phe Phe Pro Pro Ser Tyr Pro Ser Tyr Lys Leu Glu
            100                 105                 110

Asn Leu Ser Ser Ser Glu Met Gly Tyr Thr Ala Thr Leu Thr Arg Thr
        115                 120                 125

Thr Pro Thr Phe Phe Pro Lys Asp Ile Leu Thr Leu Arg Leu Asp Val
    130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro Arg Val His Ser Arg
                165                 170                 175

Ala Pro Ser Pro Leu Tyr Ser Val Glu Phe Ser Glu Glu Pro Phe Gly
            180                 185                 190
```

```
Val Ile Val His Arg Gln Leu Asp Gly Arg Val Leu Leu Asn Thr Thr
            195                 200                 205

Val Ala Pro Leu Phe Phe Ala Asp Gln Phe Leu Gln Leu Ser Thr Ser
210                 215                 220

Leu Pro Ser Gln Tyr Ile Thr Gly Leu Ala Glu His Leu Ser Pro Leu
225                 230                 235                 240

Met Leu Ser Thr Ser Trp Thr Arg Ile Thr Leu Trp Asn Arg Asp Leu
            245                 250                 255

Ala Pro Thr Pro Gly Ala Asn Leu Tyr Gly Ser His Pro Phe Tyr Leu
            260                 265                 270

Ala Leu Glu Asp Gly Gly Ser Ala His Gly Val Phe Leu Leu Asn Ser
            275                 280                 285

Asn Ala Met Asp Val Val Leu Gln Pro Ser Pro Ala Leu Ser Trp Arg
290                 295                 300

Ser Thr Gly Gly Ile Leu Asp Val Tyr Ile Phe Leu Gly Pro Glu Pro
305                 310                 315                 320

Lys Ser Val Val Gln Gln Tyr Leu Asp Val Val Gly Tyr Pro Phe Met
                325                 330                 335

Pro Pro Tyr Trp Gly Leu Gly Phe His Leu Cys Arg Trp Gly Tyr Ser
            340                 345                 350

Ser Thr Ala Ile Thr Arg Gln Val Val Glu Asn Met Thr Arg Ala His
            355                 360                 365

Phe Pro Leu Asp Val Gln Trp Asn Asp Leu Asp Tyr Met Asp Ser Arg
            370                 375                 380

Arg Asp Phe Thr Phe Asn Lys Asp Gly Phe Arg Asp Phe Pro Ala Met
385                 390                 395                 400

Val Gln Glu Leu His Gln Gly Gly Arg Arg Tyr Met Met Ile Val Asp
                405                 410                 415

Pro Ala Ile Ser Ser Ser Gly Pro Ala Gly Ser Tyr Arg Pro Tyr Asp
                420                 425                 430

Glu Gly Leu Arg Arg Gly Val Phe Ile Thr Asn Glu Thr Gly Gln Pro
            435                 440                 445

Leu Ile Gly Lys Val Trp Pro Gly Ser Thr Ala Phe Pro Asp Phe Thr
450                 455                 460

Asn Pro Thr Ala Leu Ala Trp Trp Glu Asp Met Val Ala Glu Phe His
465                 470                 475                 480

Asp Gln Val Pro Phe Asp Gly Met Trp Ile Asp Met Asn Glu Pro Ser
                485                 490                 495

Asn Phe Ile Arg Gly Ser Glu Asp Gly Cys Pro Asn Asn Glu Leu Glu
            500                 505                 510

Asn Pro Pro Tyr Val Pro Gly Val Val Gly Gly Thr Leu Gln Ala Ala
            515                 520                 525

Thr Ile Cys Ala Ser Ser His Gln Phe Leu Ser Thr His Tyr Asn Leu
530                 535                 540

His Asn Leu Tyr Gly Leu Thr Glu Ala Ile Ala Ser His Arg Ala Leu
545                 550                 555                 560

Val Lys Ala Arg Gly Thr Arg Pro Phe Val Ile Ser Arg Ser Thr Phe
                565                 570                 575

Ala Gly His Gly Arg Tyr Ala Gly His Trp Thr Gly Asp Val Trp Ser
            580                 585                 590

Ser Trp Glu Gln Leu Ala Ser Ser Val Pro Glu Ile Leu Gln Phe Asn
            595                 600                 605

Leu Leu Gly Val Pro Leu Val Gly Ala Asp Val Cys Gly Phe Leu Gly
```

-continued

```
                610                 615                 620
Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
            645                 650                 655

Pro Tyr Ser Phe Ser Glu Pro Ala Gln Gln Ala Met Arg Lys Ala Leu
                660                 665                 670

Thr Leu Arg Tyr Ala Leu Leu Pro His Leu Tyr Thr Leu Phe His Gln
            675                 680                 685

Ala His Val Ala Gly Glu Thr Val Ala Arg Pro Leu Phe Leu Glu Phe
690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
                725                 730                 735

Thr Gly Tyr Phe Pro Leu Gly Thr Trp Tyr Asp Leu Gln Thr Val Pro
            740                 745                 750

Ile Glu Ala Leu Gly Ser Leu Pro Pro Pro Ala Ala Pro Arg Glu
                755                 760                 765

Pro Ala Ile His Ser Glu Gly Gln Trp Val Thr Leu Pro Ala Pro Leu
770                 775                 780

Asp Thr Ile Asn Val His Leu Arg Ala Gly Tyr Ile Ile Pro Leu Gln
785                 790                 795                 800

Gly Pro Gly Leu Thr Thr Thr Glu Ser Arg Gln Gln Pro Met Ala Leu
                805                 810                 815

Ala Val Ala Leu Thr Lys Gly Gly Glu Ala Arg Gly Glu Leu Phe Trp
            820                 825                 830

Asp Asp Gly Glu Ser Leu Glu Val Leu Glu Arg Gly Ala Tyr Thr Gln
                835                 840                 845

Val Ile Phe Leu Ala Arg Asn Asn Thr Ile Val Asn Glu Leu Val Arg
850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
                885                 890                 895

Ser Asn Phe Thr Tyr Ser Pro Asp Thr Lys Val Leu Asp Ile Cys Val
            900                 905                 910

Ser Leu Leu Met Gly Glu Gln Phe Leu Val Ser Trp Cys
            915                 920                 925
```

<210> SEQ ID NO 16
<211> LENGTH: 952
<212> TYPE: PRT
<213> ORGANISM: artificial
<220> FEATURE:
<223> OTHER INFORMATION: hGAAwt w/sp1

<400> SEQUENCE: 16

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
                20                  25                  30

His Asp Phe Leu Leu Val Pro Arg Glu Leu Ser Gly Ser Ser Pro Val
            35                  40                  45

Leu Glu Glu Thr His Pro Ala His Gln Gln Gly Ala Ser Arg Pro Gly
```

```
            50                  55                  60
Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
                    100                 105                 110

Ala Lys Gln Gly Leu Gln Gly Ala Gln Met Gly Gln Pro Trp Cys Phe
                115                 120                 125

Phe Pro Pro Ser Tyr Pro Ser Tyr Lys Leu Glu Asn Leu Ser Ser Ser
            130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                    165                 170                 175

Asn Arg Leu His Phe Thr Ile Lys Asp Pro Ala Asn Arg Arg Tyr Glu
                180                 185                 190

Val Pro Leu Glu Thr Pro Arg Val His Ser Arg Ala Pro Ser Pro Leu
            195                 200                 205

Tyr Ser Val Glu Phe Ser Glu Glu Pro Phe Gly Val Ile Val His Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                    245                 250                 255

Ile Thr Gly Leu Ala Glu His Leu Ser Pro Leu Met Leu Ser Thr Ser
                260                 265                 270

Trp Thr Arg Ile Thr Leu Trp Asn Arg Asp Leu Ala Pro Thr Pro Gly
            275                 280                 285

Ala Asn Leu Tyr Gly Ser His Pro Phe Tyr Leu Ala Leu Glu Asp Gly
            290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                    325                 330                 335

Leu Asp Val Tyr Ile Phe Leu Gly Pro Glu Pro Lys Ser Val Val Gln
                340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
        370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
                435                 440                 445

Ser Gly Pro Ala Gly Ser Tyr Arg Pro Tyr Asp Glu Gly Leu Arg Arg
            450                 455                 460

Gly Val Phe Ile Thr Asn Glu Thr Gly Gln Pro Leu Ile Gly Lys Val
465                 470                 475                 480
```

```
Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
            835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895
```

```
Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 17
<211> LENGTH: 949
<212> TYPE: PRT
<213> ORGANISM: artificial
<220> FEATURE:
<223> OTHER INFORMATION: hGAAwt w/sp2

<400> SEQUENCE: 17

Met Pro Ser Ser Val Ser Trp Gly Ile Leu Leu Leu Ala Gly Leu Cys
1               5                   10                  15

Cys Leu Val Pro Val Ser Leu Ala Gly His Ile Leu Leu His Asp Phe
            20                  25                  30

Leu Leu Val Pro Arg Glu Leu Ser Gly Ser Ser Pro Val Leu Glu Glu
        35                  40                  45

Thr His Pro Ala His Gln Gln Gly Ala Ser Arg Pro Gly Pro Arg Asp
    50                  55                  60

Ala Gln Ala His Pro Gly Arg Pro Arg Ala Val Pro Thr Gln Cys Asp
65                  70                  75                  80

Val Pro Pro Asn Ser Arg Phe Asp Cys Ala Pro Asp Lys Ala Ile Thr
                85                  90                  95

Gln Glu Gln Cys Glu Ala Arg Gly Cys Cys Tyr Ile Pro Ala Lys Gln
            100                 105                 110

Gly Leu Gln Gly Ala Gln Met Gly Gln Pro Trp Cys Phe Phe Pro Pro
        115                 120                 125

Ser Tyr Pro Ser Tyr Lys Leu Glu Asn Leu Ser Ser Ser Glu Met Gly
    130                 135                 140

Tyr Thr Ala Thr Leu Thr Arg Thr Thr Pro Thr Phe Phe Pro Lys Asp
145                 150                 155                 160

Ile Leu Thr Leu Arg Leu Asp Val Met Met Glu Thr Glu Asn Arg Leu
                165                 170                 175

His Phe Thr Ile Lys Asp Pro Ala Asn Arg Arg Tyr Glu Val Pro Leu
            180                 185                 190

Glu Thr Pro Arg Val His Ser Arg Ala Pro Ser Pro Leu Tyr Ser Val
        195                 200                 205

Glu Phe Ser Glu Glu Pro Phe Gly Val Ile Val His Arg Gln Leu Asp
    210                 215                 220

Gly Arg Val Leu Leu Asn Thr Thr Val Ala Pro Leu Phe Phe Ala Asp
225                 230                 235                 240

Gln Phe Leu Gln Leu Ser Thr Ser Leu Pro Ser Gln Tyr Ile Thr Gly
                245                 250                 255

Leu Ala Glu His Leu Ser Pro Leu Met Leu Ser Thr Ser Trp Thr Arg
            260                 265                 270

Ile Thr Leu Trp Asn Arg Asp Leu Ala Pro Thr Pro Gly Ala Asn Leu
        275                 280                 285

Tyr Gly Ser His Pro Phe Tyr Leu Ala Leu Glu Asp Gly Gly Ser Ala
    290                 295                 300
```

```
His Gly Val Phe Leu Leu Asn Ser Asn Ala Met Asp Val Val Leu Gln
305                 310                 315                 320

Pro Ser Pro Ala Leu Ser Trp Arg Ser Thr Gly Gly Ile Leu Asp Val
            325                 330                 335

Tyr Ile Phe Leu Gly Pro Glu Pro Lys Ser Val Val Gln Gln Tyr Leu
            340                 345                 350

Asp Val Val Gly Tyr Pro Phe Met Pro Pro Tyr Trp Gly Leu Gly Phe
            355                 360                 365

His Leu Cys Arg Trp Gly Tyr Ser Ser Thr Ala Ile Thr Arg Gln Val
            370                 375                 380

Val Glu Asn Met Thr Arg Ala His Phe Pro Leu Asp Val Gln Trp Asn
385                 390                 395                 400

Asp Leu Asp Tyr Met Asp Ser Arg Arg Asp Phe Thr Phe Asn Lys Asp
            405                 410                 415

Gly Phe Arg Asp Phe Pro Ala Met Val Gln Glu Leu His Gln Gly Gly
            420                 425                 430

Arg Arg Tyr Met Met Ile Val Asp Pro Ala Ile Ser Ser Ser Gly Pro
            435                 440                 445

Ala Gly Ser Tyr Arg Pro Tyr Asp Glu Gly Leu Arg Arg Gly Val Phe
450                 455                 460

Ile Thr Asn Glu Thr Gly Gln Pro Leu Ile Gly Lys Val Trp Pro Gly
465                 470                 475                 480

Ser Thr Ala Phe Pro Asp Phe Thr Asn Pro Thr Ala Leu Ala Trp Trp
            485                 490                 495

Glu Asp Met Val Ala Glu Phe His Asp Gln Val Pro Phe Asp Gly Met
            500                 505                 510

Trp Ile Asp Met Asn Glu Pro Ser Asn Phe Ile Arg Gly Ser Glu Asp
            515                 520                 525

Gly Cys Pro Asn Asn Glu Leu Glu Asn Pro Pro Tyr Val Pro Gly Val
            530                 535                 540

Val Gly Gly Thr Leu Gln Ala Ala Thr Ile Cys Ala Ser Ser His Gln
545                 550                 555                 560

Phe Leu Ser Thr His Tyr Asn Leu His Asn Leu Tyr Gly Leu Thr Glu
            565                 570                 575

Ala Ile Ala Ser His Arg Ala Leu Val Lys Ala Arg Gly Thr Arg Pro
            580                 585                 590

Phe Val Ile Ser Arg Ser Thr Phe Ala Gly His Gly Arg Tyr Ala Gly
            595                 600                 605

His Trp Thr Gly Asp Val Trp Ser Ser Trp Glu Gln Leu Ala Ser Ser
610                 615                 620

Val Pro Glu Ile Leu Gln Phe Asn Leu Leu Gly Val Pro Leu Val Gly
625                 630                 635                 640

Ala Asp Val Cys Gly Phe Leu Gly Asn Thr Ser Glu Glu Leu Cys Val
            645                 650                 655

Arg Trp Thr Gln Leu Gly Ala Phe Tyr Pro Phe Met Arg Asn His Asn
            660                 665                 670

Ser Leu Leu Ser Leu Pro Gln Glu Pro Tyr Ser Phe Ser Glu Pro Ala
            675                 680                 685

Gln Gln Ala Met Arg Lys Ala Leu Thr Leu Arg Tyr Ala Leu Leu Pro
            690                 695                 700

His Leu Tyr Thr Leu Phe His Gln Ala His Val Ala Gly Glu Thr Val
705                 710                 715                 720

Ala Arg Pro Leu Phe Leu Glu Phe Pro Lys Asp Ser Ser Thr Trp Thr
```

```
                725                 730                 735
Val Asp His Gln Leu Leu Trp Gly Glu Ala Leu Leu Ile Thr Pro Val
            740                 745                 750

Leu Gln Ala Gly Lys Ala Glu Val Thr Gly Tyr Phe Pro Leu Gly Thr
            755                 760                 765

Trp Tyr Asp Leu Gln Thr Val Pro Ile Glu Ala Leu Gly Ser Leu Pro
        770                 775                 780

Pro Pro Pro Ala Ala Pro Arg Glu Pro Ala Ile His Ser Gly Gly Gln
785                 790                 795                 800

Trp Val Thr Leu Pro Ala Pro Leu Asp Thr Ile Asn Val His Leu Arg
                805                 810                 815

Ala Gly Tyr Ile Ile Pro Leu Gln Gly Pro Gly Leu Thr Thr Thr Glu
            820                 825                 830

Ser Arg Gln Gln Pro Met Ala Leu Ala Val Ala Leu Thr Lys Gly Gly
            835                 840                 845

Glu Ala Arg Gly Glu Leu Phe Trp Asp Asp Gly Glu Ser Leu Glu Val
        850                 855                 860

Leu Glu Arg Gly Ala Tyr Thr Gln Val Ile Phe Leu Ala Arg Asn Asn
865                 870                 875                 880

Thr Ile Val Asn Glu Leu Val Arg Val Thr Ser Glu Gly Ala Gly Leu
                885                 890                 895

Gln Leu Gln Lys Val Thr Val Leu Gly Val Ala Thr Ala Pro Gln Gln
            900                 905                 910

Val Leu Ser Asn Gly Val Pro Val Ser Asn Phe Thr Tyr Ser Pro Asp
            915                 920                 925

Thr Lys Val Leu Asp Ile Cys Val Ser Leu Leu Met Gly Glu Gln Phe
930                 935                 940

Leu Val Ser Trp Cys
945

<210> SEQ ID NO 18
<211> LENGTH: 952
<212> TYPE: PRT
<213> ORGANISM: artificial
<220> FEATURE:
<223> OTHER INFORMATION: hGAAwt w/sp1

<400> SEQUENCE: 18

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
```

```
            130                 135                 140
Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
            165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
            195                 200                 205

Tyr Ser Val Glu Phe Ser Glu Glu Pro Phe Gly Val Ile Val Arg Arg
            210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
            245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
            275                 280                 285

Ala Asn Leu Tyr Gly Ser His Pro Phe Tyr Leu Ala Leu Glu Asp Gly
            290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
            325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
            355                 360                 365

Leu Gly Phe His Leu Cys Arg Trp Gly Tyr Ser Ser Thr Ala Ile Thr
            370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
            405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
            450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
            530                 535                 540

Pro Gly Val Val Gly Gly Thr Leu Gln Ala Ala Thr Ile Cys Ala Ser
545                 550                 555                 560
```

```
Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
        660                 665                 670

Asn His Asn Ser Leu Leu Ser Leu Pro Gln Glu Pro Tyr Ser Phe Ser
    675                 680                 685

Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
        740                 745                 750

Thr Pro Val Leu Gln Ala Gly Lys Ala Glu Val Thr Gly Tyr Phe Pro
    755                 760                 765

Leu Gly Thr Trp Tyr Asp Leu Gln Thr Val Pro Val Glu Ala Leu Gly
770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
            805                 810                 815

His Leu Arg Ala Gly Tyr Ile Ile Pro Leu Gln Gly Pro Gly Leu Thr
        820                 825                 830

Thr Thr Glu Ser Arg Gln Gln Pro Met Ala Leu Ala Val Ala Leu Thr
    835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
            885                 890                 895

Ala Gly Leu Gln Leu Gln Lys Val Thr Val Leu Gly Val Ala Thr Ala
        900                 905                 910

Pro Gln Gln Val Leu Ser Asn Gly Val Pro Val Ser Asn Phe Thr Tyr
    915                 920                 925

Ser Pro Asp Thr Lys Val Leu Asp Ile Cys Val Ser Leu Leu Met Gly
930                 935                 940

Glu Gln Phe Leu Val Ser Trp Cys
945                 950

<210> SEQ ID NO 19
<211> LENGTH: 925
```

```
<212> TYPE: PRT
<213> ORGANISM: artificial
<220> FEATURE:
<223> OTHER INFORMATION: hGAAwt w/o sp

<400> SEQUENCE: 19
```

| | | | | | | | | | | | | | | |
|---|---|---|---|---|---|---|---|---|---|---|---|---|---|---|
|Gly|His|Ile|Leu|Leu|His|Asp|Phe|Leu|Val|Pro|Arg|Glu|Leu|Ser|
|1| | | |5| | | | |10| | | | |15|

Gly Ser Ser Pro Val Leu Glu Glu Thr His Pro Ala His Gln Gln Gly
                 20                  25                  30

Ala Ser Arg Pro Gly Pro Arg Asp Ala Gln Ala His Pro Gly Arg Pro
             35                  40                  45

Arg Ala Val Pro Thr Gln Cys Asp Val Pro Pro Asn Ser Arg Phe Asp
 50                  55                  60

Cys Ala Pro Asp Lys Ala Ile Thr Gln Glu Gln Cys Glu Ala Arg Gly
 65                  70                  75                  80

Cys Cys Tyr Ile Pro Ala Lys Gln Gly Leu Gln Gly Ala Gln Met Gly
                 85                  90                  95

Gln Pro Trp Cys Phe Phe Pro Pro Ser Tyr Pro Ser Tyr Lys Leu Glu
            100                 105                 110

Asn Leu Ser Ser Ser Glu Met Gly Tyr Thr Ala Thr Leu Thr Arg Thr
            115                 120                 125

Thr Pro Thr Phe Phe Pro Lys Asp Ile Leu Thr Leu Arg Leu Asp Val
130                 135                 140

Met Met Glu Thr Glu Asn Arg Leu His Phe Thr Ile Lys Asp Pro Ala
145                 150                 155                 160

Asn Arg Arg Tyr Glu Val Pro Leu Glu Thr Pro His Val His Ser Arg
                165                 170                 175

Ala Pro Ser Pro Leu Tyr Ser Val Glu Phe Ser Glu Glu Pro Phe Gly
            180                 185                 190

Val Ile Val Arg Arg Gln Leu Asp Gly Arg Val Leu Leu Asn Thr Thr
        195                 200                 205

Val Ala Pro Leu Phe Phe Ala Asp Gln Phe Leu Gln Leu Ser Thr Ser
210                 215                 220

Leu Pro Ser Gln Tyr Ile Thr Gly Leu Ala Glu His Leu Ser Pro Leu
225                 230                 235                 240

Met Leu Ser Thr Ser Trp Thr Arg Ile Thr Leu Trp Asn Arg Asp Leu
                245                 250                 255

Ala Pro Thr Pro Gly Ala Asn Leu Tyr Gly Ser His Pro Phe Tyr Leu
            260                 265                 270

Ala Leu Glu Asp Gly Gly Ser Ala His Gly Val Phe Leu Leu Asn Ser
        275                 280                 285

Asn Ala Met Asp Val Val Leu Gln Pro Ser Pro Ala Leu Ser Trp Arg
290                 295                 300

Ser Thr Gly Gly Ile Leu Asp Val Tyr Ile Phe Leu Gly Pro Glu Pro
305                 310                 315                 320

Lys Ser Val Val Gln Gln Tyr Leu Asp Val Val Gly Tyr Pro Phe Met
                325                 330                 335

Pro Pro Tyr Trp Gly Leu Gly Phe His Leu Cys Arg Trp Gly Tyr Ser
            340                 345                 350

Ser Thr Ala Ile Thr Arg Gln Val Val Glu Asn Met Thr Arg Ala His
        355                 360                 365

Phe Pro Leu Asp Val Gln Trp Asn Asp Leu Asp Tyr Met Asp Ser Arg
370                 375                 380

```
Arg Asp Phe Thr Phe Asn Lys Asp Gly Phe Arg Asp Phe Pro Ala Met
385                 390                 395                 400

Val Gln Glu Leu His Gln Gly Gly Arg Tyr Met Met Ile Val Asp
        405                 410                 415

Pro Ala Ile Ser Ser Ser Gly Pro Ala Gly Ser Tyr Arg Pro Tyr Asp
            420                 425                 430

Glu Gly Leu Arg Arg Gly Val Phe Ile Thr Asn Glu Thr Gly Gln Pro
        435                 440                 445

Leu Ile Gly Lys Val Trp Pro Gly Ser Thr Ala Phe Pro Asp Phe Thr
450                 455                 460

Asn Pro Thr Ala Leu Ala Trp Trp Glu Asp Met Val Ala Glu Phe His
465                 470                 475                 480

Asp Gln Val Pro Phe Asp Gly Met Trp Ile Asp Met Asn Glu Pro Ser
            485                 490                 495

Asn Phe Ile Arg Gly Ser Glu Asp Gly Cys Pro Asn Asn Glu Leu Glu
                500                 505                 510

Asn Pro Pro Tyr Val Pro Gly Val Val Gly Gly Thr Leu Gln Ala Ala
            515                 520                 525

Thr Ile Cys Ala Ser Ser His Gln Phe Leu Ser Thr His Tyr Asn Leu
530                 535                 540

His Asn Leu Tyr Gly Leu Thr Glu Ala Ile Ala Ser His Arg Ala Leu
545                 550                 555                 560

Val Lys Ala Arg Gly Thr Arg Pro Phe Val Ile Ser Arg Ser Thr Phe
            565                 570                 575

Ala Gly His Gly Arg Tyr Ala Gly His Trp Thr Gly Asp Val Trp Ser
        580                 585                 590

Ser Trp Glu Gln Leu Ala Ser Ser Val Pro Glu Ile Leu Gln Phe Asn
        595                 600                 605

Leu Leu Gly Val Pro Leu Val Gly Ala Asp Val Cys Gly Phe Leu Gly
610                 615                 620

Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
            645                 650                 655

Pro Tyr Ser Phe Ser Glu Pro Ala Gln Gln Ala Met Arg Lys Ala Leu
        660                 665                 670

Thr Leu Arg Tyr Ala Leu Leu Pro His Leu Tyr Thr Leu Phe His Gln
        675                 680                 685

Ala His Val Ala Gly Glu Thr Val Ala Arg Pro Leu Phe Leu Glu Phe
690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
            725                 730                 735

Thr Gly Tyr Phe Pro Leu Gly Thr Trp Tyr Asp Leu Gln Thr Val Pro
        740                 745                 750

Val Glu Ala Leu Gly Ser Leu Pro Pro Pro Ala Ala Pro Arg Glu
            755                 760                 765

Pro Ala Ile His Ser Glu Gly Gln Trp Val Thr Leu Pro Ala Pro Leu
            770                 775                 780

Asp Thr Ile Asn Val His Leu Arg Ala Gly Tyr Ile Ile Pro Leu Gln
785                 790                 795                 800

Gly Pro Gly Leu Thr Thr Thr Glu Ser Arg Gln Gln Pro Met Ala Leu
```

```
                        805                 810                 815
Ala Val Ala Leu Thr Lys Gly Gly Glu Ala Arg Gly Glu Leu Phe Trp
            820                 825                 830

Asp Asp Gly Glu Ser Leu Glu Val Leu Glu Arg Gly Ala Tyr Thr Gln
            835                 840                 845

Val Ile Phe Leu Ala Arg Asn Asn Thr Ile Val Asn Glu Leu Val Arg
    850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
                885                 890                 895

Ser Asn Phe Thr Tyr Ser Pro Asp Thr Lys Val Leu Asp Ile Cys Val
                900                 905                 910

Ser Leu Leu Met Gly Glu Gln Phe Leu Val Ser Trp Cys
            915                 920                 925

<210> SEQ ID NO 20
<211> LENGTH: 952
<212> TYPE: PRT
<213> ORGANISM: homo sapiens

<400> SEQUENCE: 20

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255
```

-continued

```
Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
```

```
                675                 680                 685
Glu Pro Ala Gln Gln Ala Met Arg Lys Ala Leu Thr Leu Arg Tyr Ala
690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 21
<211> LENGTH: 957
<212> TYPE: PRT
<213> ORGANISM: homo sapiens

<400> SEQUENCE: 21

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95
```

```
Ala Ile Thr Gln Glu Gln Cys Glu Ala Arg Gly Cys Cys Tyr Ile Pro
            100                 105                 110
Ala Lys Gln Gly Leu Gln Gly Ala Gln Met Gly Gln Pro Trp Cys Phe
        115                 120                 125
Phe Pro Pro Ser Tyr Pro Ser Tyr Lys Leu Glu Asn Leu Ser Ser Ser
    130                 135                 140
Glu Met Gly Tyr Thr Ala Thr Leu Thr Arg Thr Thr Pro Thr Phe Phe
145                 150                 155                 160
Pro Lys Asp Ile Leu Thr Leu Arg Leu Asp Val Met Met Glu Thr Glu
                165                 170                 175
Asn Arg Leu His Phe Thr Ile Lys Asp Pro Ala Asn Arg Arg Tyr Glu
            180                 185                 190
Val Pro Leu Glu Thr Pro His Val His Ser Arg Ala Pro Ser Pro Leu
        195                 200                 205
Tyr Ser Val Glu Phe Ser Glu Glu Pro Phe Gly Val Ile Val Arg Arg
    210                 215                 220
Gln Leu Asp Gly Arg Val Leu Leu Asn Thr Thr Val Ala Pro Leu Phe
225                 230                 235                 240
Phe Ala Asp Gln Phe Leu Gln Leu Ser Thr Ser Leu Pro Ser Gln Tyr
                245                 250                 255
Ile Thr Gly Leu Ala Glu His Leu Ser Pro Leu Met Leu Ser Thr Ser
            260                 265                 270
Trp Thr Arg Ile Thr Leu Trp Asn Arg Asp Leu Ala Pro Thr Pro Gly
        275                 280                 285
Ala Asn Leu Tyr Gly Ser His Pro Phe Tyr Leu Ala Leu Glu Asp Gly
    290                 295                 300
Gly Ser Ala His Gly Val Phe Leu Leu Asn Ser Asn Ala Met Asp Val
305                 310                 315                 320
Val Leu Gln Pro Ser Pro Ala Leu Ser Trp Arg Ser Thr Gly Gly Ile
                325                 330                 335
Leu Asp Val Tyr Ile Phe Leu Gly Pro Glu Pro Lys Ser Val Val Gln
            340                 345                 350
Gln Tyr Leu Asp Val Val Gly Tyr Pro Phe Met Pro Pro Tyr Trp Gly
        355                 360                 365
Leu Gly Phe His Leu Cys Arg Trp Gly Tyr Ser Ser Thr Ala Ile Thr
    370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
            420                 425                 430
Gln Gly Gly Arg Arg Tyr Met Met Ile Val Asp Pro Ala Ile Ser Ser
        435                 440                 445
Ser Gly Pro Ala Gly Ser Tyr Arg Pro Tyr Asp Glu Gly Leu Arg Arg
    450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
            500                 505                 510
Asp Gly Met Trp Ile Asp Met Asn Glu Pro Ser Asn Phe Ile Arg Gly
```

```
            515                 520                 525
Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Ala Arg Gly Pro Arg Val Leu Asp Ile Cys Val
    930                 935                 940
```

Ser Leu Leu Met Gly Glu Gln Phe Leu Val Ser Trp Cys
945                 950                 955

<210> SEQ ID NO 22
<211> LENGTH: 952
<212> TYPE: PRT
<213> ORGANISM: homo sapiens

<400> SEQUENCE: 22

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly

```
                355                 360                 365
Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                    405                 410                 415

Asn Lys Asp Gly Phe Arg Asp Phe Pro Ala Met Val Gln Glu Leu His
                420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Leu Tyr Asp Glu Gly Leu Arg Arg
        450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                    485                 490                 495

Ala Trp Trp Glu Asp Met Val Ala Glu Phe His Asp Gln Val Pro Phe
                500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
        530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                    565                 570                 575

Leu Thr Glu Ala Ile Ala Ser His Arg Ala Leu Val Lys Ala Arg Gly
                580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
        610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                    645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
        690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                    725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
        770                 775                 780
```

```
Ser Leu Pro Pro Pro Ala Ala Pro Arg Glu Pro Ala Ile His Ser
785             790             795             800

Glu Gly Gln Trp Val Thr Leu Pro Ala Pro Leu Asp Thr Ile Asn Val
                805             810             815

His Leu Arg Ala Gly Tyr Ile Ile Pro Leu Gln Gly Pro Gly Leu Thr
            820             825             830

Thr Thr Glu Ser Arg Gln Gln Pro Met Ala Leu Ala Val Ala Leu Thr
            835             840             845

Lys Gly Gly Glu Ala Arg Gly Glu Leu Phe Trp Asp Asp Gly Glu Ser
    850             855             860

Leu Glu Val Leu Glu Arg Gly Ala Tyr Thr Gln Val Ile Phe Leu Ala
865             870             875             880

Arg Asn Asn Thr Ile Val Asn Glu Leu Val Arg Val Thr Ser Glu Gly
            885             890             895

Ala Gly Leu Gln Leu Gln Lys Val Thr Val Leu Gly Val Ala Thr Ala
            900             905             910

Pro Gln Gln Val Leu Ser Asn Gly Val Pro Val Ser Asn Phe Thr Tyr
        915             920             925

Ser Pro Asp Thr Lys Val Leu Asp Ile Cys Val Ser Leu Leu Met Gly
    930             935             940

Glu Gln Phe Leu Val Ser Trp Cys
945             950
```

ACID-ALPHA GLUCOSIDASE VARIANTS AND USES THEREOF

CROSS-REFERENCE TO RELATED APPLICATION

This application is the U.S. national stage application of International Patent Application No. PCT/EP2017/072942, filed Sep. 12, 2017.

The Sequence Listing for this application is labeled "Seq-List.txt" which was created on Feb. 14, 2019 and is 95 KB. The entire content of the sequence listing is incorporated herein by reference in its entirety.

The present invention relates to variants of acid-alpha glucosidase and uses thereof. Said variants are sequence-optimized and/or are linked to heterogenous signal peptides.

Pompe disease, also known as glycogen storage disease (GSD) type II and acid maltase deficiency, is an autosomal recessive metabolic myopathy caused by a deficiency of the lysosomal enzyme acid alpha-glucosidase (GAA). GAA is an exo-1,4 and 1,6-α-glucosidase that hydrolyzes glycogen to glucose in the lysosome. Deficiency of GAA leads to glycogen accumulation in lysosomes and causes progressive damage to respiratory, cardiac, and skeletal muscle. The disease ranges from a rapidly progressive infantile course that is usually fatal by 1-2 years of age to a more slowly progressive and heterogeneous course that causes significant morbidity and early mortality in children and adults. Hirschhorn R R, The Metabolic and Molecular Bases of Inherited Disease, 3: 3389-3420 (2001, McGraw-Hill); Van der Ploeg and Reuser, Lancet 372: 1342-1351 (2008).

Current human therapy for treating Pompe disease involves administration of recombinant human GAA, otherwise termed enzyme-replacement therapy (ERT). ERT has demonstrated efficacy for severe, infantile GSD II. However the benefit of enzyme therapy is limited by the need for frequent infusions and the development of inhibitor antibodies against recombinant hGAA (Amalfitano, A., et al. (2001) Genet. In Med. 3:132-138). Furthermore, ERT does not correct efficiently the entire body, probably because of a combination of poor biodistribution of the protein following peripheral vein delivery, lack of uptake from several tissues, and high immunogenicity.

As an alternative or adjunct to ERT, the feasibility of gene therapy approaches to treat GSD-II have been investigated (Amalfitano, A., et al. (1999) Proc. Natl. Acad. Sci. USA 96:8861-8866, Ding, E., et al. (2002) Mol. Ther. 5:436-446, Fraites, T. J., et al. (2002) Mol. Ther. 5:571-578, Tsujino, S., et al. (1998) Hum. Gene Ther. 9:1609-1616). However, muscle-directed gene transfer to correct the genetic defect has to face the limitation of the systemic nature of the disease and the fact that muscle expression of a transgene tends to be more immunogenic compared with other tissues.

Doerfler et al., 2016 describe the combined administration of two constructs encoding a human codon-optimized GAA, one under the control of a liver specific promoter and the other one under the control of a muscle-specific promoter. Liver-specific promoter driven expression of GAA is employed to promote immune tolerance to GAA in a Gaa$^{-/-}$ mouse model, while muscle-specific promoter driven expression of GAA provides expression of the therapeutic protein in part of the tissues targeted for therapy. However, this strategy is not entirely satisfactory in that it requires the use of multiple constructs and it does not result in body wide expression of GAA.

Modified GAA proteins have been proposed in the past to improve lysosomal storage disease treatment. In particular, application WO2004064750 and Sun et al. 2006, disclose a chimeric GAA polypeptide comprising a signal peptide operably linked to GAA as a way to enhance targeting of the protein to the secretory pathway.

However, therapies available to the patient are not entirely satisfactory and improved GAA polypeptides and GAA production is still a need in the art. In particular, a need still exists of a long term efficacy of the treatment with GAA, of high level GAA production, of improved immunological tolerance to the produced GAA polypeptide, and of improved uptake of GAA by the cells and tissues in need thereof. In addition, in WO2004064750 and Sun et al., 2006, tissue distribution of the chimeric GAA polypeptide disclosed therein is not entirely satisfactory. Therefore, a need still exists for a GAA polypeptide that would be fully therapeutic, by allowing a correction of glycogen accumulation in most if not all tissues of interest.

SUMMARY OF THE INVENTION

The present invention relates to GAA variants that are expressed and secreted at higher levels compared to the wild type GAA protein and that elicit improved correction of the pathological accumulation of glycogen body-wide and results in the induction of immunological tolerance to GAA.

According to one aspect, the invention relates to a nucleic acid molecule comprising a nucleotide sequence having at least 85% identity to the nucleotide sequence of SEQ ID NO: 1 or SEQ ID NO:2, and which encodes a functional GAA polypeptide. In a particular embodiment of this aspect, the nucleic acid molecule comprises the nucleotide sequence shown in SEQ ID NO:1 or SEQ ID NO:2.

According to another aspect, the invention provides a nucleic acid molecule encoding a chimeric GAA polypeptide, wherein the endogenous signal peptide of the GAA protein is replaced with the signal peptide of the human alpha-1-antitrypsin (hAAT) protein. The nucleic acid molecule therefore encodes a chimeric GAA polypeptide comprising the hAAT signal peptide fused to a functional GAA polypeptide. The encoded chimeric polypeptide is a functional GAA protein wherein the amino acid sequence corresponding to the natural signal peptide of GAA is replaced by the amino acid sequence of the hAAT signal peptide. In a particular embodiment, the nucleic acid molecule of the invention encodes a chimeric polypeptide that is a functional form of the GAA polypeptide comprising a signal peptide different from that of natural GAA signal peptide, i.e. the hAAT signal peptide, and fused thereon at its N-terminal end. According to a particular embodiment, the nucleic acid molecule of the invention comprises a nucleotide sequence encoding the amino acid sequence of the hAAT signal peptide of SEQ ID NO:4. In a further embodiment, the GAA coding sequence is a sequence optimized for transgene expression in vivo.

In yet another aspect, the invention provides a nucleic acid construct comprising the nucleic acid molecule of the invention. The nucleic acid construct of the invention may be an expression cassette. The expression cassette may comprise the nucleic acid molecule of the invention operably linked to one or more regulatory sequences such as a promoter, an intron, a polyadenylation signal and/or an enhancer (for example a cis-regulatory motif, or CRM). Illustrative promoters include liver-specific promoters such as a promoter selected in the group consisting of the alpha-1-antitrypsin promoter (hAAT), the transthyretin promoter, the albumin promoter and the thyroxine-binding globulin (TBG) promoter. In another particular embodiment, the promoter is a muscle-specific promoter, such as the Spc5-12, MCK and desmin promoters. In another embodiment, the promoter is an ubiquitous promoter such as the CMV, CAG and PGK promoters. The nucleic acid construct of the invention may further comprise an intron, in particular an intron selected in the group consisting of a human beta globin b2 (or HBB2) intron, a FIX intron and a chicken beta-globin intron and a SV40 intron. In addition, the intron may be a modified intron such as a modified HBB2 intron of SEQ ID NO:8, a modified FIX intron of SEQ ID NO:10, or a modified chicken beta-globin intron of SEQ ID NO:12. In a specific embodiment of the invention, the nucleic acid construct of the invention comprises, preferably in this order: an enhancer; an intron; a promoter, in particular a liver-specific promoter; the nucleic acid sequence encoding the chimeric GAA polypeptide; and a polyadenylation signal. In a specific embodiment, the nucleic acid construct of the invention comprises, in particular in this order: an ApoE control region; a HBB2 intron, in particular a modified HBB2 intron; the hAAT promoter; the nucleic acid molecule encoding the chimeric GAA polypeptide; and a bovine growth hormone polyadenylation signal. In a particular embodiment, the nucleic acid construct comprises the nucleotide sequence of SEQ ID NO:13 or SEQ ID NO:14.

In a further aspect, the invention also provides a vector comprising the nucleic acid molecule or the nucleic acid construct as defined above. In a particular embodiment, the vector is a viral vector, in particular a retroviral vector, such as a lentiviral vector, or an AAV vector. In particular, the viral vector is an AAV vector. Illustrative AAV vectors that may be implemented in the present invention include AAV vectors having a capsid from the AAV1, AAV2, variant AAV2, AAV3, variant AAV3, AAV3B, variant AAV3B, AAV4, AAV5, AAV6, variant AAV6, AAV7, AAV8, AAV9, AAV10 such as AAVcy10 and AAVrh10, AAVrh74, AAVdj, AAV-Anc80, AAV-LK03, AAV2i8, and porcine AAV, such as AAVpo4 and AAVpo6, serotype. More specifically, the AAV vector has an AAV8, AAV9, AAVrh74 or AAV2i8 capsid, in particular an AAV8, AAV9 or AAVrh74 capsid, more particularly an AAV8 capsid.

Furthermore, the invention provides a cell comprising a nucleic acid molecule, a nucleic acid construct or a vector as described above. The cell may be, for example, a liver or muscle cell.

According to another aspect, the invention also provides a chimeric GAA polypeptide encoded by the nucleic acid molecule as herein described.

A further object of the invention is a pharmaceutical composition comprising, in a pharmaceutically acceptable carrier, the nucleic acid molecule of the invention, the nucleic acid construct of the invention, the vector of the invention, the cell of the invention, or the chimeric GAA polypeptide of the invention.

The invention also provides the nucleic acid molecule, the nucleic acid construct, the vector, the cell or a chimeric GAA polypeptide as described above, for use as a medicament.

The invention also provides the nucleic acid molecule, the nucleic acid construct, the vector, the cell or the chimeric GAA polypeptide as described above, for use in a method for treating a glycogen storage disease. In a particular embodiment, the glycogen storage disease is GSDI, GSDII, GSDIII, GSDIV, GSDV, GSDVI, GSDVI, GSDVIII or lethal congenital glycogen storage disease of the heart. In a more particular embodiment, the glycogen storage disease is selected in the group consisting of GSDI, GSDII and GSDIII, more particularly in the group consisting of GSDII and GSDIII. In an even more particular embodiment, the glycogen storage disease is GSDII.

LEGENDS TO THE FIGURES

FIG. 1. Combination of sequence optimization and an efficient signal peptide increases secretion of hGAA in vitro. Human hepatoma cells (Huh7) were transfected by Lipofectamine™ with a control plasmid (GFP), a plasmid expressing wild-type hGAA under the transcriptional control of a liver specific promoter. The hGAA transgene carried either the native signal peptide (pAAV-LSP-sp1-hGAA) or the signal peptide of alpha-1 antitrypsin (pAAV-LSP-sp2-hGAA). The same cDNAs encoding sp1-hGAA and sp2-hGAA were also sequence optimized (pAAV-hAAT-sp1-hGAAco1 and pAAV-hAAT-sp2-hGAAco1, respectively). 48 hours after transfection the activity of hGAA in the culture media was measured by a fluorogenic enzymatic assay and GAA activity evaluated against a standard curve of recombinant hGAA. The histogram plot shows the average±SD of the fold increase of the levels of secreted hGAA normalized for the levels measured in hGAA or hGAAco1 fused with sp1 signal peptide. Data derived from three different experiments. Statistical analysis has been performed by paired t-test (*=$p<0.05$ as indicated).

Figure 2:
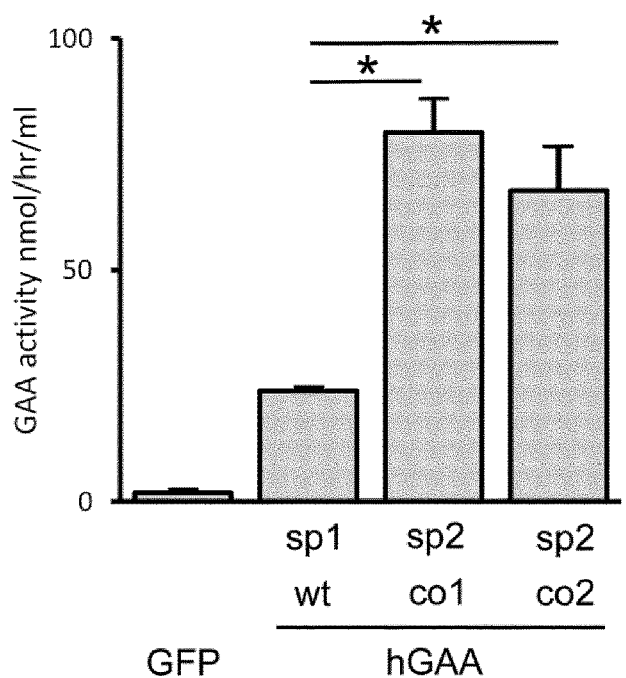

FIG. 2. Combination of different sequence optimization algorithms of hGAA sequence and an efficient signal peptide significantly increases secretion in vitro. Human hepatoma cells (Huh7) were transfected by Lipofectamine™ with a control plasmid (GFP), a plasmid expressing wild-type hGAA (wt) under the transcriptional control of a liver specific promoter fused with sp1 signal peptide or hGAA sequence optimized following two different algorithms (co1 and co2 respectively) fused with sp2. 48 hours after transfection the activity of hGAA in the culture media was measured by a fluorogenic enzymatic assay. The histogram plot shows the average±SE of the levels of secreted hGAA deriving from three different experiments. Statistical analysis has been performed by ANOVA (*=$p<0.05$ vs sp1 wt).

DETAILED DESCRIPTION OF THE INVENTION

An aspect of the invention relates to a nucleic acid molecule comprising a nucleotide sequence having at least 85% identity to the nucleotide sequence of SEQ ID NO: 1 or SEQ ID NO:2 and which encodes a functional GAA polypeptide. SEQ ID NO:1 and SEQ ID NO:2 are optimized nucleic acid sequences coding for a natural, wild-type, hGAA polypeptide in its precursor form (i.e. it encodes hGAA without its signal peptide).

Lysosomal acid α-glucosidase or "GAA" (E.C. 3.2. 1.20) (1,4-α-D-glucan glucohydrolase), is an exo-1,4-α-D-glucosidase that hydrolyses both α-1,4 and α-1,6 linkages of oligosaccharides to liberate glucose. A deficiency in GAA results in glycogen storage disease type II (GSDII), also referred to as Pompe disease (although this term formally refers to the infantile onset form of the disease). It catalyzes the complete degradation of glycogen with slowing at branching points. The 28 kb human acid α-glucosidase gene on chromosome 17 encodes a 3.6 kb mRNA which produces a 951 amino acid polypeptide (Hoefsloot et al., (1988) EMBO J. 7: 1697; Martiniuk et al., (1990) DNA and Cell Biology 9: 85). The enzyme receives co-translational N-linked glycosylation in the endoplasmic reticulum. It is synthesized as a 110-kDa precursor form, which matures by extensive glycosylation modification, phosphorylation and by proteolytic processing through an approximately 90-kDa endosomal intermediate into the final lysosomal 76 and 67 kDa forms (Hoefsloot, (1988) EMBO J. 7: 1697; Hoefsloot et al., (1990) Biochem. J. 272: 485; Wisselaar et al., (1993) J. Biol. Chem. 268: 2223; Hermans et al., (1993) Biochem. J. 289: 681).

In patients with GSD II, a deficiency of acid α-glucosidase causes massive accumulation of glycogen in lysosomes, disrupting cellular function (Hirschhorn, R. and Reuser, A. J. (2001), in The Metabolic and Molecular Basis for Inherited Disease, (eds, Scriver, C. R. et al.) pages 3389-3419 (McGraw-Hill, New York). In the most common infantile form, patients exhibit progressive muscle degeneration and cardiomyopathy and die before two years of age. Severe debilitation is present in the juvenile and adult onset forms.

Furthermore, patients having other GSDs may benefit from the administration of an optimized form of GAA. For example, it has been shown (Sun et al. (2013) Mol Genet Metab 108(2): 145; WO2010/005565) that administration of GAA reduces glycogen in primary myoblasts from glycogen storage disease type III (GSD III) patients.

The term "GAA" or "GAA polypeptide", as used herein, encompasses mature (~76 or ~67 kDa) and precursor (e.g., ~110 kDa) GAA, in particular the precursor form, as well as modified or mutated by insertion(s), deletion (s) and/or substitution(s)) GAA proteins or fragments thereof that are functional derivatives of GAA, i.e. that retain biological function of GAA (i.e., have at least one biological activity of the native GAA protein, e.g., can hydrolyze glycogen, as defined above) and GAA variants (e.g., GAA II as described by Kunita et al., (1997) Biochemica et Biophysica Acta 1362: 269; GAA polymorphisms and SNPs are described by Hirschhorn, R. and Reuser, A. J. (2001) In The Metabolic and Molecular Basis for Inherited Disease (Scriver, C. R., Beaudet, A. L., Sly, W. S. & Valle, D. Eds.), pp. 3389-3419. McGraw-Hill, New York, see pages 3403-3405). Any GAA coding sequence known in the art may be used, for example, see SEQ ID NO:3; GenBank Accession number NM_00152 and Hoefsloot et al., (1988) EMBO J. 7: 1697 and Van Hove et al., (1996) Proc. Natl. Acad. Sci. USA 93: 65 (human), GenBank Accession number NM_008064 (mouse), and Kunita et al., (1997) Biochemica et Biophysica Acta 1362: 269 (quail).

The coding sequence of the GAA polypeptide can be derived from any source, including avian and mammalian species. The term "avian" as used herein includes, but is not limited to, chickens, ducks, geese, quail, turkeys and pheasants. The term "mammal" as used herein includes, but is not limited to, humans, simians and other non-human primates, bovines, ovines, caprines, equines, felines, canines, lagomorphs, etc. In embodiments of the invention, the nucleic acids of the invention encode a human, mouse or quail, in particular a human, GAA polypeptide. In a further particular embodiment, the GAA polypeptide encoded by the nucleic acid molecule of the invention comprises the amino acid sequence shown in SEQ ID NO:15 or 19, which corresponds to two variants of hGAA without their signal peptide (of note, the natural signal peptide of hGAA corresponds to amino acid 1-27 in SEQ ID NO:16 or in SEQ ID NO:18 which corresponds to the two variants of hGAA of SEQ ID NO:15 and 19, but including their natural signal peptide). Thus, in a particular embodiment of the invention, the GAA polypeptide encoded by the nucleic acid of the invention comprises the amino acid sequence shown in SEQ ID NO:4 fused to the amino acid sequence of SEQ ID NO:19 or of SEQ ID NO: 15.

The nucleic acid molecule of the invention preferably has at least 85 percent, more preferably at least 90 percent, and even more preferably at least 92 percent identity, in particular at least 95 percent identity, for example at least 98, 99 or 100 percent identity to the nucleotide sequence of SEQ ID NO: 1 or SEQ ID NO:2.

In another embodiment of the invention, the nucleic acid molecule of the invention has at least 75 percent (such as at least 77%), at least 80 percent or at least 82 percent (such as at least 83%) identity to nucleotides 82-2859 of the sequence shown in SEQ ID NO:3, which is the sequence of a wild-type hGAA coding sequence (nucleotides 1-81 being the part encoding for the natural signal peptide of hGAA).

The term "identical" and declinations thereof refers to the sequence identity between two nucleic acid molecules. When a position in both of the two compared sequences is occupied by the same base e.g., if a position in each of two DNA molecules is occupied by adenine, then the molecules are identical at that position. The percent of identity between two sequences is a function of the number of matching positions shared by the two sequences divided by the number of positions compared×100. For example, if 6 of 10 of the positions in two sequences are matched then the two sequences are 60% identical. Generally, a comparison is made when two sequences are aligned to give maximum identity. Various bioinformatic tools known to the one skilled in the art might be used to align nucleic acid sequences such as BLAST or FASTA.

In a particular embodiment, the nucleic acid molecule of the invention comprises a nucleic acid sequence encoding a functional GAA that comprises, consists essentially of or consists of the nucleic acid sequence shown in SEQ ID NO:1 or SEQ ID NO:2.

Furthermore, the nucleic acid molecule of the invention encodes a functional GAA protein, i.e. it encodes for a human GAA protein that, when expressed, has the functionality of wild-type GAA protein. As defined above, the functionality of wild-type GAA is to hydrolyse both α-1,4 and α-1,6 linkages of oligosaccharides and polysaccharides, more particularly of glycogen, to liberate glucose. The functional GAA protein encoded by the nucleic acid of the invention may have a hydrolysing activity on glycogen of at least 50%, 60%, 70%, 80%, 90%, 95%, 99%, or at least 100% as compared to the wild-type GAA protein encoded by the nucleic acid sequence of SEQ ID NO:1 to 3. The activity of the GAA protein encoded by the nucleic acid of the invention may even be of more than 100%, such as of more than 110%, 120%, 130%, 140%, or even more than 150% of the activity of the wild-type GAA protein encoded by the nucleic acid sequence of SEQ ID NO:1 to 3.

A skilled person is readily able to determine whether a nucleic acid according to the invention expresses a functional GAA protein. Suitable methods would be apparent to those skilled in the art. For example, one suitable in vitro method involves inserting the nucleic acid into a vector, such as a plasmid or viral vector, transfecting or transducing host cells, such as 293T or HeLa cells, or other cells such as Huh7, with the vector, and assaying for GAA activity. Alternatively, a suitable in vivo method involves transducing a vector containing the nucleic acid into a mouse model of Pompe disease or another glycogen storage disorder and assaying for functional GAA in the plasma of the mouse and presence of GAA in tissues. Suitable methods are described in more details in the experimental part below.

The inventors have found that the above described nucleic acid molecule causes surprisingly high levels of expression of functional GAA protein compared to the wild-type GAA cDNA. This means that this nucleic acid molecule may be used to produce high levels of GAA protein and is of special interest in contexts where GAA expression and/or activity is deficient or where high levels of expression of GAA can ameliorate a disease, such as for glycogen storage disease. In a particular, the glycogen storage disease may be GSDI (von Gierke's disease), GSDII (Pompe disease), GSDIII (Cori disease), GSDIV, GSDV, GSDVI, GSDVII, GSDVIII or lethal congenital glycogen storage disease of the heart. More particularly, the glycogen storage disease is selected in the group consisting of GSDI, GSDII and GSDIII, even more particularly in the group consisting of GSDII and GSDIII. In an even more particular embodiment, the glycogen storage disease is GSDII. In particular, the nucleic acid molecules of the invention may be useful in gene therapy to treat GAA-deficient conditions, or other conditions associated by accumulation of glycogen such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII. In an even more particular embodiment, the nucleic acid molecules of the invention may be useful in gene therapy to treat GSDII.

The sequence of the nucleic acid molecule of the invention, encoding a functional GAA, is optimized for expression of the GAA polypeptide in vivo. Sequence optimization may include a number of changes in a nucleic acid sequence, including codon optimization, increase of GC content, decrease of the number of CpG islands, decrease of the number of alternative open reading frames (ARFs) and decrease of the number of splice donor and splice acceptor sites. Because of the degeneracy of the genetic code, different nucleic acid molecules may encode the same protein. It is also well known that the genetic codes of different organisms are often biased towards using one of the several codons that encode the same amino acid over the others. Through codon optimization, changes are introduced in a nucleotide sequence that take advantage of the codon bias existing in a given cellular context so that the resulting codon optimized nucleotide sequence is more likely to be expressed in such given cellular context at a relatively high level compared to the non-codon optimised sequence. In a preferred embodiment of the invention, such sequence optimized nucleotide sequence encoding a functional GAA is codon-optimized to improve its expression in human cells compared to non-codon optimized nucleotide sequences coding for the same GAA protein, for example by taking advantage of the human specific codon usage bias.

In a particular embodiment, the optimized GAA coding sequence is codon optimized, and/or has an increased GC content and/or has a decreased number of alternative open reading frames, and/or has a decreased number of splice donor and/or splice acceptor sites, as compared to nucleotides 82-2859 of the wild-type hGAA coding sequence of SEQ ID NO:3. For example, nucleic acid sequence of the invention results in an at least 2, 3, 4, 5 or 10% increase of GC content in the GAA sequence as compared to the sequence of the wild-type GAA sequence. In a particular embodiment, the nucleic acid sequence of the invention results in a 2, 3, 4 or, more particularly, 5% or 10% (particularly 5%) increase of GC content in the GAA sequence as compared to the sequence of the wild-type GAA nucleotide sequence. In a particular embodiment, the nucleic acid sequence of the invention encoding a functional GAA polypeptide is "substantially identical", that is, about 70% identical, more preferably about 80% identical, even more preferably about 90% identical, even more preferably about 95% identical, even more preferably about 97%, 98% or even 99% identical to nucleotides 82-2859 of the sequence shown in SEQ ID NO: 3. As mentioned above, in addition to the GC content and/or number of ARFs, sequence optimization may also comprise a decrease in the number of CpG islands in the sequence and/or a decrease in the number of splice donor and acceptor sites. Of course, as is well known to those skilled in the art, sequence optimization is a balance between all these parameters, meaning that a sequence may be considered optimized if at least one of the above parameters is improved while one or more of the other parameters is not, as long as the optimized sequence leads to an improvement of the transgene, such as an improved expression and/or a decreased immune response to the transgene in vivo.

In addition, the adaptiveness of a nucleotide sequence encoding a functional GAA to the codon usage of human cells may be expressed as codon adaptation index (CAI). A codon adaptation index is herein defined as a measurement of the relative adaptiveness of the codon usage of a gene towards the codon usage of highly expressed human genes. The relative adaptiveness (w) of each codon is the ratio of the usage of each codon, to that of the most abundant codon for the same amino acid. The CAI is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al, Gene. 1997, 199:293-301; zur Megede et al, Journal of Virology, 2000, 74: 2628-2635). Preferably, a nucleic acid molecule encoding a GAA has a CAI of at least 0.75 (in particular 0.77), 0.8, 0.85, 0.90, 0.92 or 0.94.

In one embodiment, the nucleic acid molecule of the invention encodes a protein having between 0 and 50, between 0 and 30, between 0 and 20, between 0 and 15, between 0 and 10, or between 0 and 5 amino acid changes to the protein encoded by the nucleotide sequence of SEQ ID NO: 1 or SEQ ID NO:2. Furthermore, the GAA protein encoded by the nucleic acid of the invention may be a variant of GAA known in the art wherein the nucleic acid molecule of the invention encodes a protein having between 0 and 50, between 0 and 30, between 0 and 20, between 0 and 15, between 0 and 10, or between 0 and 5 amino acid changes to the GAA protein known in the art. Such GAA protein known in the art that may serve as the basis for designing a functional variant of a GAA protein may be found in particular in the Uniprot entry of GAA (accession number P10253; corresponding to GenBank CAA68763.1; SEQ ID NO:16). In a further particular embodiment, the GAA moiety of the nucleic acid sequence of the invention encodes variants GAA polypeptides, or functional variants of such peptides as defined herein, such as those selected in the group consisting of the polypeptides identified as Genbank Accession Numbers AAA52506.1 (SEQ ID NO:20), EAW89583.1 (SEQ ID NO:21) and ABI53718.1 (SEQ ID NO:22). Other variant GAA polypeptides include those described in WO2012/145644, WO00/34451 and U.S. Pat. No. 6,858,425. In a particular embodiment, the nucleic acid molecule of the invention encodes a parent GAA polypeptide which is derived from the amino acid sequence shown in SEQ ID NO: 16 or SEQ ID NO:18.

In a particular embodiment, the GAA polypeptide encoded by the nucleic acid molecule of the invention is a functional GAA and has a sequence identity to amino acid residues 28-952 of the hGAA protein shown in SEQ ID NO:16 or SEQ ID NO:18 of at least 80%, in particular at least 85%, 90%, 95%, more particularly at least 96%, 97%, 98%, or 99%. In a particular embodiment, the GAA protein encoded by the nucleic acid molecule of the invention has the sequence of amino acid residues 28-952 of SEQ ID NO:16 or SEQ ID NO:18.

The term "nucleic acid sequence" (or nucleic acid molecule) refers to a DNA or RNA molecule in single or double stranded form, particularly a DNA encoding a GAA polypeptide according to the invention.

The invention also relates to a nucleic acid molecule encoding a chimeric functional GAA polypeptide comprising a hAAT signal peptide linked to a GAA polypeptide.

In particular, the inventors have further surprisingly shown that the combination of sequence optimisation and signal peptide replacement results in the production of higher expression levels and higher secretion of functional protein. Therefore, the nucleic acid molecule of the invention may encode a chimeric GAA polypeptide, wherein said nucleic acid molecule comprises two moieties:
a moiety encoding a signal peptide (otherwise referred to as "signal peptide moiety"), and
a moiety encoding a functional GAA polypeptide as defined above.

In the chimeric GAA polypeptide encoded by the nucleic acid molecule of the invention, the signal peptide moiety encodes a signal peptide of the hAAT protein. In a particular embodiment, the nucleic acid molecule of the invention may be an optimized sequence coding for a chimeric GAA polypeptide comprising a signal peptide of hAAT operably linked to a GAA polypeptide.

As compared to a wild-type GAA polypeptide, the endogenous signal peptide of wild-type GAA is replaced with an exogenous signal peptide, i.e. a signal peptide derived from a protein different from GAA which is a signal peptide of hAAT. The exogenous signal peptide fused to the remainder of the GAA protein increases the secretion of the resulting chimeric GAA polypeptide as compared to the corresponding GAA polypeptide comprising its natural signal peptide. Furthermore, according to a particular embodiment of the invention, the nucleotide sequence corresponding to the signal peptide of the hAAT protein may be an optimized sequence as provided above.

The relative proportion of newly-synthesized GAA that is secreted from the cell can be routinely determined by methods known in the art and as described in the examples. Secreted proteins can be detected by directly measuring the protein itself (e.g., by Western blot) or by protein activity assays (e.g., enzyme assays) in cell culture medium, serum, milk, etc.

Those skilled in the art will further understand that the chimeric GAA polypeptide can contain additional amino acids, e.g., as a result of manipulations of the nucleic acid construct such as the addition of a restriction site, as long as these additional amino acids do not render the signal peptide or the GAA polypeptide non-functional. The additional amino acids can be cleaved or can be retained by the mature polypeptide as long as retention does not result in a non-functional polypeptide.

The invention also relates to a nucleic acid construct comprising a nucleic acid molecule of the invention. The nucleic acid construct may correspond to an expression cassette comprising the nucleic acid sequence of the invention, operably linked to one or more expression control sequences and/or other sequences improving the expression of a transgene and/or sequences enhancing the secretion of the encoded protein and/or sequences enhancing the uptake of the encoded protein. As used herein, the term "operably linked" refers to a linkage of polynucleotide elements in a functional relationship. A nucleic acid is "operably linked" when it is placed into a functional relationship with another nucleic acid sequence. For instance, a promoter, or another transcription regulatory sequence, is operably linked to a coding sequence if it affects the transcription of the coding sequence. Such expression control sequences are known in the art, such as promoters, enhancers (such as cis-regulatory modules (CRM)), introns, polyA signals, etc.

In particular, the expression cassette may include a promoter. The promoter may be an ubiquitous or tissue-specific promoter, in particular a promoter able to promote expression in cells or tissues in which expression of GAA is desirable such as in cells or tissues in which GAA expression is desirable in GAA-deficient patients. In a particular embodiment, the promoter is a liver-specific promoter such as the alpha-1 antitrypsin promoter (hAAT) (SEQ ID NO:5), the transthyretin promoter, the albumin promoter, the thyroxine-binding globulin (TBG) promoter, the LSP promoter (comprising a thyroid hormone-binding globulin promoter sequence, two copies of an alpha1-microglobulin/bikunin enhancer sequence, and a leader sequence—34.Ill , C. R., et al. (1997). Optimization of the human factor VIII complementary DNA expression plasmid for gene therapy of hemophilia A. Blood Coag. Fibrinol. 8: S23S30.), etc. Other useful liver-specific promoters are known in the art, for example those listed in the Liver Specific Gene Promoter Database compiled the Cold Spring Harbor Laboratory (rulai.cshl.edu/LSPD/). A preferred promoter in the context of the invention is the hAAT promoter. In another embodiment, the promoter is a promoter directing expression in one tissue or cell of interest (such as in muscle cells), and in liver cells. For example, to some extent, promoters specific of muscle cells such as the desmin, Spc5-12 and MCK promoters may present some leakage of expression into liver cells, which can be advantageous to induce immune tolerance of the subject to the GAA protein expressed from the nucleic acid of the invention.

Other tissue-specific or non-tissue-specific promoters may be useful in the practice of the invention. For example, the expression cassette may include a tissue-specific promoter which is a promoter different from a liver specific promoter. For example the promoter may be muscle-specific, such as the desmin promoter (and a desmin promoter variant such as a desmin promoter including natural or artificial enhancers), the SPc5-12 or the MCK promoter. In another embodiment, the promoter is a promoter specific of other cell lineage, such as the erythropoietin promoter, for the expression of the GAA polypeptide from cells of the erythroid lineage.

In another embodiment, the promoter is an ubiquitous promoter. Representative ubiquitous promoters include the cytomegalovirus enhancer/chicken beta actin (CAG) promoter, the cytomegalovirus enhancer/promoter (CMV), the PGK promoter, the SV40 early promoter, etc.

In addition, the promoter may also be an endogenous promoter such as the albumin promoter or the GAA promoter.

In a particular embodiment, the promoter is associated to an enhancer sequence, such as a cis-regulatory module (CRMs) or an artificial enhancer sequence. For example, the promoter may be associated to an enhancer sequence such as the human ApoE control region (or Human apolipoprotein E/C-I gene locus, hepatic control region HCR-1—Genbank accession No. U32510, shown in SEQ ID NO:6). In a particular embodiment, an enhancer sequence such as the ApoE sequence is associated to a liver-specific promoter such as those listed above, and in particular such as the hAAT promoter. Other CRMs useful in the practice of the present invention include those described in Rincon et al., Mol Ther. 2015 January; 23(1):43-52, Chuah et al., Mol Ther. 2014 September; 22(9):1605-13 or Nair et al., Blood. 2014 May 15; 123(20):3195-9.

In another particular embodiment, the nucleic acid construct comprises an intron, in particular an intron placed between the promoter and the GAA coding sequence. An intron may be introduced to increase mRNA stability and the production of the protein. In a further embodiment, the nucleic acid construct comprises a human beta globin b2 (or HBB2) intron, a coagulation factor IX (FIX) intron, a SV40 intron or a chicken beta-globin intron. In another further embodiment, the nucleic acid construct of the invention contains a modified intron (in particular a modified HBB2 or FIX intron) designed to decrease the number of, or even totally remove, alternative open reading frames (ARFs) found in said intron. Preferably, ARFs are removed whose length spans over 50 bp and have a stop codon in frame with a start codon. ARFs may be removed by modifying the sequence of the intron. For example, modification may be carried out by way of nucleotide substitution, insertion or deletion, preferably by nucleotide substitution. As an illustration, one or more nucleotides, in particular one nucleotide, in an ATG or GTG start codon present in the sequence of the intron of interest may be replaced resulting in a non-start codon. For example, an ATG or a GTG may be replaced by a CTG, which is not a start codon, within the sequence of the intron of interest.

The classical HBB2 intron used in nucleic acid constructs is shown in SEQ ID NO:7. For example, this HBB2 intron may be modified by eliminating start codons (ATG and GTG codons) within said intron. In a particular embodiment, the modified HBB2 intron comprised in the construct has the sequence shown in SEQ ID NO:8. The classical FIX intron used in nucleic acid constructs is derived from the first intron of human FIX and is shown in SEQ ID NO:9. FIX intron may be modified by eliminating start codons (ATG and GTG codons) within said intron. In a particular embodiment, the modified FIX intron comprised in the construct of the invention has the sequence shown in SEQ ID NO:10. The classical chicken-beta globin intron used in nucleic acid constructs is shown in SEQ ID NO:11. Chicken-beta globin intron may be modified by eliminating start codons (ATG and GTG codons) within said intron. In a particular embodiment, the modified chicken-beta globin intron comprised in the construct of the invention has the sequence shown in SEQ ID NO:12.

The inventors have previously shown in WO2015/162302 that such a modified intron, in particular a modified HBB2 or FIX intron, has advantageous properties and can significantly improve the expression of a transgene.

In a particular embodiment, the nucleic acid construct of the invention is an expression cassette comprising, in the 5' to 3' orientation, a promoter optionally preceded by an enhancer, the coding sequence of the invention (i.e. the optimized GAA coding sequence of the invention, the chimeric GAA coding sequence of the invention, or the chimeric and optimized GAA coding sequence of the invention), and a polyadenylation signal (such as the bovine growth hormone polyadenylation signal, the SV40 polyadenylation signal, or another naturally occurring or artificial polyadenylation signal). In a particular embodiment, the nucleic acid construct of the invention is an expression cassette comprising, in the 5' to 3' orientation, a promoter optionally preceded by an enhancer, (such as the ApoE control region), an intron (in particular an intron as defined above), the coding sequence of the invention, and a polyadenylation signal. In a further particular embodiment, the nucleic acid construct of the invention is an expression cassette comprising, in the 5' to 3' orientation, an enhancer such as the ApoE control region, a promoter, an intron (in particular an intron as defined above), the coding sequence of the invention, and a polyadenylation signal. In a further particular embodiment of the invention the expression cassette comprising, in the 5' to 3' orientation, an ApoE control region, the hAAT-liver specific promoter, a HBB2 intron (in particular a modified HBB2 intron as defined above), the coding sequence of the invention, and the bovine growth hormone polyadenylation signal, such as the nucleic acid construct shown in SEQ ID NO:13 and SEQ ID NO:14, which includes the sequence-optimized GAA nucleic acid molecule of SEQ ID NO:1 and SEQ ID NO:2, respectively.

In a particular embodiment, the expression cassette comprises the ApoE control region, the hAAT-liver specific promoter, a codon-optimized HBB2 intron, the coding sequence of the invention and the bovine growth hormone polyadenylation signal.

In designing the nucleic acid construct of the invention, one skilled in the art will take care of respecting the size limit of the vector used for delivering said construct to a cell or organ. In particular, one skilled in the art knows that a major limitation of AAV vector is its cargo capacity which may vary from one AAV serotype to another but is thought to be limited to around the size of parental viral genome. For example, 5 kb is the maximum size usually thought to be packaged into an AAV8 capsid. (Wu Z. et al., Mol Ther., 2010, 18(1): 80-86; Lai Y. et al., Mol Ther., 2010, 18(1): 75-79; Wang Y. et al., Hum Gene Ther Methods, 2012, 23(4): 225-33). Accordingly, those skilled in the art will take care in practicing the present invention to select the components of the nucleic acid construct of the invention so that the resulting nucleic acid sequence, including sequences coding AAV 5'- and 3'-ITRs to preferably not exceed 110% of the cargo capacity of the AAV vector implemented, in particular to preferably not exceed 5.5 kb.

The invention also relates to a vector comprising a nucleic acid molecule or construct as disclosed herein. In particular, the vector of the invention is a vector suitable for protein expression, preferably for use in gene therapy. In one embodiment, the vector is a plasmid vector. In another embodiment, the vector is a nanoparticle containing a nucleic acid molecule of the invention, in particular a messenger RNA encoding the GAA polypeptide of the invention. In another embodiment, the vector is a system based on transposons, allowing integration of the nucleic acid molecule or construct of the invention in the genome of the target cell, such as the hyperactive Sleeping Beauty (SB100X) transposon system (Mates et al. 2009). In another embodiment, the vector is a viral vector suitable for gene therapy, targeting any cell of interest such as liver tissue or cells, muscle cell, CNS cells (such as brain cells), or hematopoietic stem cells such as cells of the erythroid lineage (such as erythrocytes). In this case, the nucleic acid construct of the invention also contains sequences suitable for producing an efficient viral vector, as is well known in the art. In a particular embodiment, the viral vector is derived from an integrating virus. In particular, the viral vector may be derived from a retrovirus or a lentivirus. In a further particular embodiment, the viral vector is an AAV vector, such as an AAV vector suitable for transducing liver tissues or cells, more particularly an AAV-1, -2 and AAV-2 variants (such as the quadruple-mutant capsid optimized AAV-2 comprising an engineered capsid with Y44+500+ 730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as -cy10 and -rh10, -rh74, -dj, Anc80, LK03, AAV2i8, porcine AAV serotypes such as AAVpo4 and AAVpo6, etc., vector or a retroviral vector such as a lentiviral vector and an alpha-retrovirus. As is known in the art, depending on the specific viral vector considered for use, additional suitable sequences will be introduced in the nucleic acid construct of the invention for obtaining a functional viral vector. Suitable sequences include AAV ITRs for an AAV vector, or LTRs for lentiviral vectors. As such, the invention also relates to an expression cassette as described above, flanked by an ITR or an LTR on each side.

Advantages of viral vectors are discussed in the following part of this disclosure. Viral vectors are preferred for delivering the nucleic acid molecule or construct of the invention, such as a retroviral vector, for example a lentiviral vector, or a non-pathogenic parvovirus, more preferably an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter).

Therefore, AAV vectors have arisen considerable interest as potential vectors for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV-1, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as cy10 and -rh10, -rh74, -dj, Anc80, LK03, AAV2i8, porcine AAV serotypes such as AAVpo4 and AAVpo6, and tyrosine, lysine and serine capsid mutants of the AAV serotypes, etc. In addition, other non-natural engineered variants and chimeric AAV can also be useful.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells. Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

Accordingly, the present invention relates to an AAV vector comprising the nucleic acid molecule or construct of the invention. In the context of the present invention, the AAV vector comprises an AAV capsid able to transduce the target cells of interest, in particular hepatocytes. According to a particular embodiment, the AAV vector is of the AAV-1, -2, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24(6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -10 such as -cy10 and -rh10, -rh74, -dj, Anc80, LK03, AAV2i8, porcine AAV such as AAVpo4 and AAVpo6, and tyrosine, lysine and serine capsid mutants of a AAV serotypes, etc., serotype. In a particular embodiment, the AAV vector is of the AAV8, AAV9, AAVrh74 or AAV2i8 serotype (i.e. the AAV vector has a capsid of the AAV8, AAV9, AAVrh74 or AAV2i8 serotype). In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype. For example, the genome of the pseudotyped vector may have a capsid derived from the AAV8, AAV9, AAVrh74 or AAV2i8 serotype, and its genome may be derived from and different serotype. In a particular embodiment, the AAV vector has a capsid of the AAV8, AAV9 or AAVrh74 serotype, in particular of the AAV8 or AAV9 serotype, more particularly of the AAV8 serotype.

In a specific embodiment, wherein the vector is for use in delivering the transgene to muscle cells, the AAV vector may be selected, among others, in the group consisting of AAV8, AAV9 and AAVrh74.

In another specific embodiment, wherein the vector is for use in delivering the transgene to liver cells, the AAV vector may be selected, among others, in the group consisting of AAV5, AAV8, AAV9, AAV-LK03, AAV-Anc80 and AAV3B.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example a chimeric AAV vector can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In addition, capsid variants may include single amino acid changes such as tyrosine mutants (e.g. as described in Zhong et al., 2008).

In addition, the genome of the AAV vector may either be a single stranded or self-complementary double-stranded genome (McCarty et al., Gene Therapy, 2003). Self-complementary double-stranded AAV vectors are generated by deleting the terminal resolution site (trs) from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid.

In a particularly preferred embodiment, the invention relates to an AAV vector comprising, in a single-stranded or double-stranded, self-complementary genome (e.g. a single-stranded genome), the nucleic acid construct of the invention. In one embodiment, the AAV vector comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid. In a further particular embodiment, said nucleic acid is operably linked to a promoter, especially an ubiquitous or liver-specific promoter. According to a specific variant embodiment, the promoter is an ubiquitous promoter such as the cytomegalovirus enhancer/chicken beta actin (CAG) promoter, the cytomegalovirus enhancer/promoter (CMV), the PGK promoter and the SV40 early promoter. In a specific variant, the ubiquitous promoter is the CAG promoter. According to another variant, the promoter is a liver-specific promoter such as the alpha-1 antitrypsin promoter (hAAT), the transthyretin promoter, the albumin promoter and the thyroxine-binding globulin (TBG) promoter. In a specific variant, the liver-specific promoter is the hAAT liver-specific promoter of SEQ ID NO:5. In a further particular embodiment, the nucleic acid construct comprised into the genome of the AAV vector of the invention further comprises an intron as described above, such as an intron placed between the promoter and the nucleic acid sequence encoding the GAA coding sequence (i.e. the optimized GAA coding sequence of the invention, the chimeric GAA coding sequence of the invention, or the chimeric and optimized GAA coding sequence of the invention). Representative introns that may be included within the nucleic acid construct introduced within the AAV vector genome include, without limitation, the human beta globin b2 (or HBB2) intron, the FIX intron and the chicken beta-globin intron. Said intron within the genome of the AAV vector may be a classical (or unmodified) intron or a modified intron designed to decrease the number of, or even totally remove, alternative open reading frames (ARFs) within said intron. Modified and unmodified introns that may be used in the practice of this embodiment where the nucleic acid of the invention is introduced within an AAV vector are thoroughly described above. In a particular embodiment, the AAV vector, in particular an AAV vector comprising an AAV8, AAV9, AAVrh74 or AAV2i8 capsid, in particular an AAV8, AAV9 or AAVrh74 capsid, such as an AAV8 or AAV9 capsid, more particularly an AAV8 capsid, of the invention includes within its genome a modified (or optimized) intron such as the modified HBB2 intron of SEQ ID NO:8, the modified FIX intron of SEQ ID NO:10 and the modified chicken beta-globin intron of SEQ ID NO:12. In a further particular embodiment, the vector of the invention is an AAV vector comprising comprises an AAV8, AAV9, AAVrh74 or AAV2i8 capsid, in particular an AAV8, AAV9 or AAVrh74 capsid, such as an AAV8 or AAV9 capsid, more particularly an AAV8 capsid, comprising a genome containing, in the 5' to 3' orientation: an AAV 5'-ITR (such as an AAV2 5'-ITR); an ApoE control region; the hAAT-liver specific promoter; a HBB2 intron (in particular a modified HBB2 intron as defined above); the GAA coding sequence of the invention; the bovine growth hormone polyadenylation signal; and an AAV 3'-ITR (such as an AAV2 3'-ITR), such as a genome comprising a the nucleic acid construct shown in SEQ ID NO:13 flanked by an AAV 5'-ITR (such as an AAV2 5'-ITR) and an AAV 3'-ITR (such as an AAV2 3'-ITR).

In a particular embodiment of the invention, the nucleic acid construct of the invention comprises a liver-specific promoter as described above, and the vector is a viral vector capable of transducing liver tissue or cells as described above. The protolerogenic and metabolic properties of the liver are advantageously implemented thanks to this embodiment to develop highly efficient and optimized vectors to express secretable forms of GAA in hepatocytes and to induce immune tolerance to the protein.

In addition, in a further particular embodiment, the invention provides the combination of two vectors, such as two viral vectors, in particular two AAV vectors, for improving gene delivery and treatment efficacy in the cells of interest. For example, the two vectors may carry the nucleic acid molecule of the invention coding for the GAA protein of the invention, under the control of one different promoter in each of these two vectors. In a particular embodiment, one vector comprises a promoter which is a liver-specific promoter (as one of those described above), and the other vector comprises a promoter which is specific of another tissue of interest for the treatment of a glycogen storage disorder, such as a muscle-specific promoter, for example the desmin promoter. In a particular variant of this embodiment, this combination of vectors corresponds to multiple co-packaged AAV vectors produced as described in WO2015196179.

In another aspect, the invention provides a chimeric GAA polypeptide, wherein the naturally occurring GAA signal peptide is replaced with the signal peptide of the hAAT protein. In a particular embodiment, the chimeric GAA polypeptide has the sequence shown in SEQ ID NO:17, or is a functional derivative thereof having at least 90% identity, in particular at least 95%, at least 96%, at least 97%, at least 98%, or at least 99% identity to the sequence shown in SEQ ID NO:17.

The invention also relates to a cell, for example a liver cell, that is transformed with a nucleic acid molecule or construct of the invention as is the case for ex vivo gene therapy. Cells of the invention may be delivered to the subject in need thereof, such as GAA-deficient patient, by any appropriate administration route such as via injection in the liver or in the bloodstream of said subject. In a particular embodiment, the invention involves introducing the nucleic acid of the invention into liver cells, in particular into liver cells of the subject to be treated, and administering said transformed liver cells into which the nucleic acid has been introduced to the subject. Advantageously, this embodiment is useful for secreting GAA from said cells. In a particular embodiment, the liver cells are liver cells from the patient to be treated, or are liver stem cells that are further transformed, and differentiated in vitro into liver cells, for subsequent administration to the patient.

The present invention further relates to a transgenic, nonhuman animal comprising in its genome the nucleic acid molecule or construct encoding a GAA protein according to the invention. In a particular embodiment, the animal is a mouse.

Apart from the specific delivery systems embodied below in the examples, various delivery systems are known and can be used to administer the nucleic acid molecule or construct of the invention, e.g., encapsulation in liposomes, microparticles, microcapsules, recombinant cells capable of expressing the coding sequence of the invention, receptor-mediated endocytosis, construction of a therapeutic nucleic acid as part of a retroviral or other vector, etc.

According to an embodiment, it may be desirable to introduce the chimeric GAA polypeptide, nucleic acid molecule, nucleic acid construct or cell of the invention into the liver of the subject by any suitable route. In addition naked DNA such as minicircles and transposons can be used for delivery or lentiviral vectors. Additionally, gene editing technologies such as zinc finger nucleases, meganucleases, TALENs, and CRISPR can also be used to deliver the coding sequence of the invention.

The present invention also provides pharmaceutical compositions comprising the nucleic acid molecule, the nucleic acid construct, the vector, the chimeric GAA polypeptide, or the cell of the invention. Such compositions comprise a therapeutically effective amount of the therapeutic (the nucleic acid molecule, the nucleic acid construct, the vector, the chimeric GAA polypeptide or the cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid, vector or cell of the invention is formulated in a composition comprising phosphate-buffered saline and supplemented with 0.25% human serum albumin. In another particular embodiment, the nucleic acid, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

In an embodiment, the nucleic acid molecule, the nucleic acid construct, the vector, the chimeric GAA polypeptide or the cell of the invention can be delivered in a vesicle, in particular a liposome. In yet another embodiment, the nucleic acid molecule, the nucleic acid construct, the vector, the chimeric GAA polypeptide or the cell of the invention can be delivered in a controlled release system.

Methods of administration of the nucleic acid molecule, the nucleic acid construct, the vector, the chimeric GAA polypeptide or the cell of the invention include but are not limited to intradermal, intramuscular, intraperitoneal, intravenous, subcutaneous, intranasal, epidural, and oral routes. In a particular embodiment, the administration is via the intravenous or intramuscular route. The nucleic acid molecule, the nucleic acid construct, the vector, the chimeric GAA polypeptide or the cell of the invention, whether vectorized or not, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment, e.g. the liver. This may be achieved, for example, by means of an implant, said implant being of a porous, nonporous, or gelatinous material, including membranes, such as sialastic membranes, or fibers.

The amount of the therapeutic (i.e. the nucleic acid molecule, the nucleic acid construct, the vector, the chimeric GAA polypeptide or the cell of the invention) of the invention which will be effective in the treatment of a glycogen storage disease can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the nucleic acid molecule, the nucleic acid construct, the vector, the chimeric GAA polypeptide or the cell of the invention administered to the subject in need thereof will vary based on several factors including, without limitation, the route of administration, the specific disease treated, the subject's age or the level of expression necessary to obtain the therapeutic effect. One skilled in the art can readily determine, based on its knowledge in this field, the dosage range required based on these factors and others. In case of a treatment comprising administering a viral vector, such as an AAV vector, to the subject, typical doses of the vector are of at least $1 \times 10^8$ vector genomes per kilogram body weight (vg/kg), such as at least $1 \times 10^9$ vg/kg, at least $1 \times 10^{10}$ vg/kg, at least $1 \times 10^{11}$ vg/kg, at least $1 \times 10^{12}$ vg/kg at least $1 \times 10^{13}$ vg/kg, or at least $1 \times 10^{14}$ vg/kg.

The invention also relates to a method for treating a glycogen storage disease, which comprises a step of delivering a therapeutic effective amount of the nucleic acid, the vector, the chimeric polypeptide, the pharmaceutical composition or the cell of the invention to a subject in need thereof.

The invention also relates to a method for treating a glycogen storage disease, said method inducing no immune response to the transgene (i.e. to the chimeric GAA polypeptide of the invention), or inducing a reduced immune response to the transgene, comprising a step of delivering a therapeutic effective amount of the nucleic acid molecule, nucleic acid construct, vector, pharmaceutical composition or cell of the invention to a subject in need thereof. The invention also relates to a method for treating a glycogen storage disease, said method comprising repeated administration of a therapeutic effective amount of the nucleic acid molecule, nucleic acid construct, vector, pharmaceutical composition or cell of the invention to a subject in need thereof. In this aspect, the nucleic acid molecule or the nucleic acid construct of the invention comprises a promoter which is functional in liver cells, thereby allowing immune tolerance to the expressed chimeric GAA polypeptide produced therefrom. As well, in this aspect, the pharmaceutical composition used in this aspect comprises a nucleic acid molecule or nucleic acid construct comprising a promoter which is functional in liver cells. In case of delivery of liver cells, said cells may be cells previously collected from the subject in need of the treatment and that were engineered by introducing therein the nucleic acid molecule or the nucleic acid construct of the invention to thereby make them able to produce the chimeric GAA polypeptide of the invention. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a viral vector of the invention is done using a different virus for each successive administration, thereby avoiding a reduction of efficacy because of a possible immune response against a previously administered viral vector. For example, a first administration of a viral vector comprising an AAV8 capsid may be done, followed by the administration of a vector comprising an AAV9 capsid, or even by the administration of a virus unrelated to AAVs, such as a retroviral or lentiviral vector.

The invention also relates to a method for treating a glycogen storage disease, said method inducing no immune response to the transgene (i.e. to the chimeric GAA polypeptide of the invention), or inducing a reduced immune response to the transgene, comprising a step of delivering a therapeutic effective amount of the nucleic acid molecule, nucleic acid construct, vector, pharmaceutical composition or cell of the invention to a subject in need thereof. The transgene may be used to produce high levels of GAA protein, and provides therapeutic benefits such as avoiding to resort to immunosuppressive treatments, allowing low dose immunosuppressive treatment, and allowing repeated administration of the nucleic acid molecule of the invention to a subject in need thereof. Therefore, the nucleic acid molecule of the invention is of special interest in contexts where GAA protein induces an immune response or GAA expression and/or activity is deficient or where high levels of expression of GAA can ameliorate a disease, such as for a glycogen storage disease. The invention also relates to a method for treating a glycogen storage disease, said method comprising repeated administration of a therapeutic effective amount of the nucleic acid molecule, nucleic acid construct, vector, pharmaceutical composition or cell of the invention to a subject in need thereof. In this aspect, the nucleic acid molecule or the nucleic acid construct of the invention comprises a promoter which is functional in liver cells, thereby allowing immune tolerance to the expressed chimeric GAA polypeptide produced therefrom. As well, in this aspect, the pharmaceutical composition used in this aspect comprises a nucleic acid molecule or nucleic acid construct comprising a promoter which is functional in liver cells. In case of delivery of liver cells, said cells may be cells previously collected from the subject in need of the treatment and that were engineered by introducing therein the nucleic acid molecule or the nucleic acid construct of the invention to thereby make them able to produce the chimeric GAA polypeptide of the invention. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a viral vector of the invention is done using a different virus for each successive administration, thereby avoiding a reduction of efficacy because of a possible immune response against a previously administered viral vector. For example, a first administration of a viral vector comprising an AAV8 capsid may be done, followed by the administration of a vector comprising an AAV9 capsid, or even by the administration of a virus unrelated to AAVs, such as a retroviral or lentiviral vector.

According to the present invention, a treatment may include curative, alleviation or prophylactic effects. Accordingly, therapeutic and prophylactic treatment includes amelioration of the symptoms of a particular glycogen storage disease or preventing or otherwise reducing the risk of developing a particular glycogen storage disease. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition. The term 'treatment' is used herein to refer to any regimen that can benefit an animal, in particular a mammal, more particularly a human subject.

The invention also relates to an ex vivo gene therapy method for the treatment of a glycogen storage disease, comprising introducing the nucleic acid molecule or the nucleic acid construct of the invention into an isolated cell of a patient in need thereof, for example an isolated hematopoietic stem cell, and introducing said cell into said patient in need thereof. In a particular embodiment of this aspect, the nucleic acid molecule or construct is introduced into the cell with a vector as defined above. In a particular embodiment, the vector is an integrative viral vector. In a further particular embodiment, the viral vector is a retroviral vector, such as a lenviral vector. For example, a lentiviral vector as disclosed in van Til et al., 2010, Blood, 115(26), p. 5329, may be used in the practice in the method of the present invention.

The invention also relates to the nucleic acid molecule, the nucleic acid construct, the vector, the chimeric GAA polypeptide or the cell of the invention for use as a medicament.

The invention also relates to the nucleic acid molecule, the nucleic acid construct, the vector, the chimeric GAA polypeptide or the cell of the invention, for use in a method for treating a disease caused by a mutation in the GAA gene, in particular in a method for treating Pompe disease. The invention further relates to the nucleic acid molecule, the nucleic acid construct, the vector, the chimeric GAA polypeptide or the cell of the invention, for use in a method for treating a glycogen storage disease, such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII. The chimeric GAA polypeptide of the invention may be administered to a patient in need thereof, for use in enzyme replacement therapy (ERT), such as for use in enzyme replacement therapy of one of a glycogen storage disease, such as GSDIII (Cori's disease) but also for GSD-IV, -VI, -IX, -XI and cardiac glycogenosis due to AMP-activated protein kinase gamma subunit 2 deficiency.

The invention further relates to the use of the nucleic acid molecule, the nucleic acid construct, the vector, the chimeric GAA polypeptide or the cell of the invention, in the manufacture of a medicament useful for treating a glycogen storage disease, such as GSDI (von Gierke's disease), GSDII (Pompe disease), GSDIII (Cori disease), GSDIV, GSDV, GSDVI, GSDVII, GSDVIII and lethal congenital glycogen storage disease of the heart, more particularly GSDI, GSDII or GSDIII, even more particularly GSDII and GSDIII, and most particularly GSDII.

EXAMPLES

The invention is further described in detail by reference to the following experimental examples and the attached figures. These examples are provided for purposes of illustration only, and are not intended to be limiting.

Material and Methods

GAA Activity

GAA activity was measured following homogenization of frozen tissue samples in distilled water. 50-100 mg of tissue were weighed and homogenized, then centrifuged for 20 minutes at 10000×g. The reaction was set up with 10 µl of supernatant and 20 µl of substrate—4MUα-D-glucoside, in a 96 wells plate. The reaction mixture was incubated at 37° C. for one hour, and then stopped by adding 150 µl of Sodium Carbonate buffer pH 10.5. A standard curve (0-2500 pmol/µl of 4MU) was used to measure released fluorescent 4MU from individual reaction mixture, using the EnSpire alpha plate reader (Perkin-Elmer) at 449 nm (Emission) and 360 nm (Excitation). The protein concentration of the clarified supernatant was quantified by BCA (Thermo Fisher Scientific). To calculate the GAA activity, released 4MU concentration was divided by the sample protein concentration and activity was reported as nmol/hour/mg protein.

Results

To increase the secretion of human GAA (hGAA), we combined transgene sequence optimization with a signal peptide derived from a protein highly secreted in the liver. We compared five different constructs:

1. pAAV-LSP-sp1-hGAA: plasmid expressing human GAA with the wild-type signal peptide (sp1) under the transcriptional control of a liver specific promoter (LSP) composed by the alpha1-microglobulin enhancer and the thyroxine binding globulin promoter.
2. pAAV-LSP-sp2-hGAA: plasmid expressing human GAA with the human alpha-1-antitrypsin signal peptide (sp2) under the transcriptional control of the LSP.
3. pAAV-hAAT-sp1-hGAAco1: plasmid expressing the sequence optimized version of hGAA (hGAAco1) with the native signal peptide sp1 under the transcriptional control of the human alpha-1-anti-trypsin Apolipoprotein E hepatocyte control region enhancer (hAAT) promoter.
4. pAAV-hAAT-sp2-hGAAco1: plasmid expressing the sequence optimized version of hGAA (hGAAco1) with the alpha-1-antitrypsin signal peptide sp2 under the transcriptional control of hAAT promoter.
5. pAAV-hAAT-sp2-hGAAco2: plasmid expressing a different sequence optimized version of hGAA (hGAAco2) with the alpha-1-antitrypsin signal peptide sp2 under the transcriptional control of hAAT promoter.

Amino acids 1-27 (here defined as sp1) of the wild type hGAA sequence were replaced by amino acids 1-24 (here defined as sp2) of the sequence of the human alpha-1-antitrypsin (NP_000286.3). The hGAA sequence was optimized following two different algorithms (resulting in sequences co1 and co2 respectively). We first evaluated in vitro the hGAA secretion efficiency of the first four constructs described above. Plasmids were transfected in Huh-7 cells, a hepatoma-derived cell line. 48 hours after transfection we measured the activity of hGAA in the medium. The data indicates that the addition of sp2 signal peptide to the wild-type hGAA sequence does not change its secretion profile. Surprisingly when the same strategy has been applied to the optimized hGAA sequence we observed a statistically significant increase in the secretion (FIG. 1). These data indicate that the combination of an efficient signal peptide and sequence optimization increases the secretion of hGAA. We then compared in vitro the hGAA secretion level obtained with two optimized hGAA sequences. We transfected Huh-7 cells with plasmids expressing wild-type hGAA or hGAA sequence-optimized following two distinct algorithms (co1 and co2 respectively) fused with the sp2 signal peptide. 48 hours after the transfection we measured the level of hGAA in the culture media. We observed increased levels of hGAA in the media of cells transfected with hGAA expressing plasmids. Surprisingly, both constructs bearing optimized hGAA fused with sp2 shown significantly increased hGAA secretion in the media. No significant difference have been observed between this two constructs (p=0.187). These data indicate that the combination of an efficient signal peptide with two different optimized sequences improves the secretion of hGAA. Notably, although the two optimized sequences have different characteristics in terms of GC content, alternative open reading frames, alternative splicing sites, and CAI, they show a similar efficacy in vitro (Table 1).

TABLE 1

Description of the optimized sequences. Table illustrating the characteristics of the two hGAA optimized sequences compared to the wild-type one.

| sequence | WT | co1 | co2 |
|---|---|---|---|
| CAI[a] | 0.84 | 0.94 | 0.77 |
| GC content[b] | 64.7 | 61.9 | 54.4 |
| aORF 5'→3'[c] | 2 | 3 | 0 |
| aORF 3'→5'[d] | 5 | 4 | 0 |
| SA[e] | 3 | 0 | 1 |
| SD[f] | 3 | 0 | 0 |
| % identity vs wt[g] | | 83.1 | 77.7 |
| % identity vs co1[h] | | | 80.8 |
| CpG islands[i] | 4 | 5 | 1 |

[a]codon adaptation index and
[b]GC content calculated using a rare codon analysis tool (see Worldwide Website: genscript.com).
[c]and [d]are respectively the alternative open reading frames calculated on the 5' to 3' (aORF 5'→3')and 3' to 5' (aORF 3'→5')strands.
[e]and [f]are respectively the acceptor (SA) and donor (SD) splicing sites calculated using a splicing site online prediction tool (see Worldwide Website: fruitfly.org/seq_tools/splice.html).
[g]and [h]are respectively the percentual identity calculated versus wild-type (wt) and optimized co1 sequence.
[i]CpG islands calculated using MethDB online tool (see Worldwide Website: methdb.de/links.html). CpG islands are sequences longer than 100 bp, with GC content > 60% and an observed/expected ratio > 0.6.

In addition, whether liver transduction with our vectors induce a humoral response against the transgene is tested. Mice are injected intravenously with AAV8 vectors expressing hGAAco1 or hGAAco2 fused with sp2, under the transcriptional control of a liver specific promoter. Mice injected intramuscularly with an AAV9 expressing hGAAco under the transcriptional control of a constitutive promoter (CAG, chicken beta actin promoter and cytomegalovirus enhancer) show very high levels of total IgG specific to the hGAA transgene, whereas vectors expressing the same protein in the liver show lower levels of humoral responses to the hGAA transgene. These data indicate that the expression of a transgene in the liver is fundamental for the induction of peripheral tolerance. They provide indications that highly secretable hGAA transgenes are less immunogenic than their wild type counterpart.

The invention claimed is:

1. A nucleic acid molecule encoding a functional chimeric acid alpha-glucosidase (GAA) polypeptide having acid alpha-glucosidase activity, comprising the signal peptide of the human alpha-1-antitrypsin protein fused to the functional GAA polypeptide having acid alpha-glucosidase activity, wherein the functional GAA polypeptide having acid alpha-glucosidase activity is encoded by a nucleotide sequence having at least 85% identity to SEQ ID NO: 1 or SEQ ID NO: 2.

2. The nucleic acid molecule according to claim 1, wherein the nucleotide sequence encoding the functional GAA polypeptide having acid alpha-glucosidase activity comprises SEQ ID NO: 1 or SEQ ID NO: 2.

3. A nucleic acid construct, comprising the nucleic acid molecule according to claim 1, which is an expression cassette comprising said nucleic acid molecule operably linked to a promoter wherein said nucleic acid construct optionally further comprises an intron, wherein said intron is optionally a modified intron.

4. The nucleic acid construct according to claim 3, comprising: an enhancer; an intron; a promoter, the nucleic acid molecule encoding the chimeric GAA polypeptide having acid alpha-glucosidase activity; and a polyadenylation signal.

5. The nucleic acid construct according to claim 4, comprising: an ApoE control region; a HBB2 intron; the hAAT promoter; the nucleic acid molecule encoding the chimeric GAA polypeptide having acid alpha-glucosidase activity; and a bovine growth hormone polyadenylation signal.

6. A vector comprising the nucleic acid molecule according to claim 1.

7. The vector according to claim 6, which is a single-stranded or double-stranded self-complementary AAV vector.

8. The vector according to claim 7, wherein the AAV vector has an AAV8, AAV9, AAVrh74 or AAV2i8 capsid.

9. A cell transformed with the nucleic acid molecule according to claim 1.

* * * * *

UNITED STATES PATENT AND TRADEMARK OFFICE
CERTIFICATE OF CORRECTION

| | | |
|---|---|---|
| PATENT NO. | : 11,421,211 B2 | Page 1 of 1 |
| APPLICATION NO. | : 16/332373 | |
| DATED | : August 23, 2022 | |
| INVENTOR(S) | : Federico Mingozzi et al. | |

It is certified that error appears in the above-identified patent and that said Letters Patent is hereby corrected as shown below:

In the Specification

Column 3,
Line 63, "GSDVI, GSDVI, GSDVIII" should read --GSDVI, GSDVII, GSDVIII--.

Column 10,
Line 27, "S23S30.)," should read --S23-S30.),--.

Signed and Sealed this
Fifteenth Day of August, 2023

Katherine Kelly Vidal
*Director of the United States Patent and Trademark Office*